US011419926B2

(12) United States Patent
Glorioso, III et al.

(10) Patent No.: US 11,419,926 B2
(45) Date of Patent: *Aug. 23, 2022

(54) IDENTIFICATION OF MUTATIONS IN HERPES SIMPLEX VIRUS ENVELOPE GLYCOPROTEINS THAT ENABLE OR ENHANCE VECTOR RETARGETING TO NOVEL NON-HSV RECEPTORS

(71) Applicant: University of Pittsburgh—Of the Commonwealth System of Higher Education, Pittsburgh, PA (US)

(72) Inventors: Joseph C. Glorioso, III, Pittsburgh, PA (US); Hiroaki Uchida, Hachioji (JP); Justus B. Cohen, Allison Park, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 331 days.

This patent is subject to a terminal disclaimer.

(21) Appl. No.: 16/417,254

(22) Filed: May 20, 2019

(65) Prior Publication Data

US 2020/0147189 A1 May 14, 2020

Related U.S. Application Data

(63) Continuation of application No. 15/409,245, filed on Jan. 18, 2017, now Pat. No. 10,328,136, which is a continuation of application No. 15/137,953, filed on Apr. 25, 2016, now abandoned, which is a continuation of application No. 13/641,649, filed as application No. PCT/US2011/032923 on Apr. 18, 2011, now Pat. No. 9,593,347.

(60) Provisional application No. 61/325,137, filed on Apr. 16, 2010.

(51) Int. Cl.
| | |
|---|---|
| *A61K 35/763* | (2015.01) |
| *C12N 15/869* | (2006.01) |
| *C12N 15/38* | (2006.01) |
| *A61K 48/00* | (2006.01) |
| *A61K 35/00* | (2006.01) |
| *A61K 39/00* | (2006.01) |
| *C07K 14/005* | (2006.01) |
| *C12N 7/00* | (2006.01) |
| *C12N 15/86* | (2006.01) |

(52) U.S. Cl.
CPC .......... *A61K 39/001104* (2018.08); *A61K 39/001159* (2018.08); *A61K 39/001182* (2018.08); *C07K 14/005* (2013.01); *C12N 7/00* (2013.01); *C12N 15/86* (2013.01); *C12N 15/8695* (2013.01); *A61K 2039/585* (2013.01); *C12N 2710/16621* (2013.01); *C12N 2710/16622* (2013.01); *C12N 2710/16643* (2013.01); *C12N 2710/16671* (2013.01); *C12N 2810/6009* (2013.01); *C12N 2810/851* (2013.01); *C12N 2810/859* (2013.01)

(58) Field of Classification Search
None
See application file for complete search history.

(56) References Cited

U.S. PATENT DOCUMENTS

| | | | |
|---|---|---|---|
| 5,059,538 A | 10/1991 | Nozaki et al. | |
| 5,759,814 A | 6/1998 | Burke et al. | |
| 5,804,413 A | 9/1998 | DeLuca | |
| 5,849,572 A | 12/1998 | Glorioso et al. | |
| 5,879,934 A | 3/1999 | DeLuca | |
| 6,261,552 B1 | 7/2001 | DeLuca | |
| 6,469,155 B1 | 10/2002 | Fiume et al. | |
| 6,653,447 B1 | 11/2003 | Cosman et al. | |
| 7,473,418 B2 | 1/2009 | Yu et al. | |
| 7,514,252 B2 | 4/2009 | Chiocca et al. | |
| 7,531,167 B2 | 5/2009 | Glorioso et al. | |
| 8,129,167 B2 | 3/2012 | Cosman | |
| 8,957,036 B2 | 2/2015 | Cascio et al. | |
| 9,157,071 B2 | 10/2015 | Campadelli et al. | |
| 9,593,347 B2 | 3/2017 | Glorioso, III et al. | |
| 10,172,893 B2* | 1/2019 | Uchida ............ | A61P 35/00 |
| 10,576,115 B2* | 3/2020 | Uchida ............ | A61P 35/00 |
| 2002/0037575 A1 | 3/2002 | Speck | |
| 2008/0008686 A1 | 1/2008 | Yao | |

(Continued)

FOREIGN PATENT DOCUMENTS

| | | |
|---|---|---|
| JP | 2001-508294 A | 6/2001 |
| JP | 2003-518080 A | 6/2003 |

(Continued)

OTHER PUBLICATIONS

Shi et al, Identification of 22 Novel Motifs of the Cell Entry Fusion Glycoprotein B of Oncolytic Herpes Simplex Viruses: Sequence Analysis and Literature, Review. Front. Oncol. 10:1386, pp. 1-14.*

(Continued)

*Primary Examiner* — Maria Marvich
(74) *Attorney, Agent, or Firm* — Leydig, Voit & Mayer

(57) ABSTRACT

In one embodiment, the invention provides an HSV vector comprising a mutant gB and/or a mutant gH glycoprotein, where the viral envelope further comprises a non-native ligand specific for a protein present on the surface of a predetermined cell type. In another embodiment, the invention provides an HSV vector comprising (a) a mutant gC and/or gD envelope glycoprotein which comprises a non-native ligand specific for a protein present on the surface of a predetermined cell type; and (b) a mutant envelope glycoprotein other than gD.

15 Claims, 9 Drawing Sheets

Figure 1:
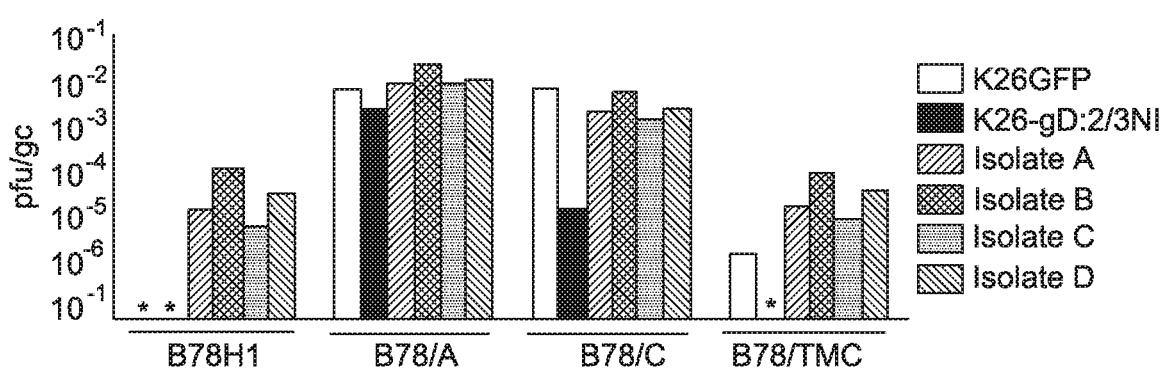

Specification includes a Sequence Listing.

(56) References Cited

U.S. PATENT DOCUMENTS

| | | | |
|---|---|---|---|
| 2008/0289058 | A1 | 11/2008 | Cascio et al. |
| 2009/0136452 | A1 | 5/2009 | Zhou et al. |
| 2010/0041737 | A1 | 2/2010 | Naldini et al. |
| 2010/0233141 | A1 | 9/2010 | Polach et al. |
| 2011/0213017 | A1 | 9/2011 | Cascio et al. |
| 2013/0071430 | A1 | 3/2013 | Nakamura et al. |
| 2013/0096186 | A1 | 4/2013 | Glorioso, III et al. |
| 2013/0156808 | A1 | 6/2013 | Jonjic |
| 2016/0153000 | A1 | 6/2016 | Glorioso et al. |
| 2016/0250267 | A1 | 9/2016 | Uchida et al. |
| 2017/0035819 | A1 | 2/2017 | Uchida et al. |
| 2017/0274025 | A1 | 3/2017 | Cascio et al. |
| 2017/0081384 | A1 | 4/2017 | Glorioso, III et al. |
| 2017/0107537 | A1 | 7/2017 | Glorioso, III et al. |
| 2017/0189514 | A1 | 9/2017 | Uchida et al. |

FOREIGN PATENT DOCUMENTS

| | | |
|---|---|---|
| KR | 2003-0047667 A | 6/2003 |
| WO | WO 99/06583 A1 | 2/1999 |
| WO | WO 2008/141151 A2 | 11/2008 |
| WO | WO 2008/143875 A1 | 11/2008 |
| WO | WO 2009/111892 A1 | 9/2009 |
| WO | WO 2009/144755 A1 | 12/2009 |
| WO | WO 2009/148488 A2 | 12/2009 |
| WO | WO 2009/150431 A1 | 12/2009 |
| WO | WO 2011/125469 A1 | 10/2011 |
| WO | WO 2011/130749 A2 | 10/2011 |
| WO | WO 2012/006181 A2 | 1/2012 |
| WO | WO 2015/009952 A1 | 1/2015 |
| WO | WO 2015/066042 A1 | 5/2015 |

OTHER PUBLICATIONS

Shanks et al, Are animal models predictive for humans?Philosophy, Ethics, and Humanities in Medicine 2009, pp. 1-20.*

Zheng et al, Oncolytic Viruses for Cancer Therapy: Barriers and Recent Advances, Molecular Therapy, 2019, pp. 234-247.*

Ma et al, Oncolytic herpes simplex virus and immunotherapy, Immunology (2018) 19:40, pp. 1-11.*

Adamiak et al., "Herpes Simplex Virus Type 2 Glycoprotein G is Targeted by the Sulfated Oligo- and Polysaccharide Inhibitors of Virus Attachment to Cells," *Journal of Virology*, 81(24), 13424-13434 (2007).

Aghi et al., "Oncolytic herpes virus with defective ICP6 specifically replicates in quiescent cells with homozygous genetic mutations in p16," *Oncogene*, 27: 4249-4254 (2008).

Akimoto et al., "A new delivery system for 5-fluorouracil using prodrug and converting enzyme," *J. Ophthalmol.*, 86(5): 581-586 (2002).

Amelio et al., "A Chromatin Insulator-Like Element in the Herpes Simplex Virus Type 1 Latency-Associated Transcript Region Binds CCCTC-Binding Factor and Displays Enhancer-Blocking and Silencing Activities," *J. of Virology*, 80(5): 2358-2368 (Mar. 2006).

Anderson et al., "Pseudotyping of Glycoprotein D-Deficient Herpes Simplex Virus Type 1 with Vesicular Stomatitis Virus Glycoprotein G Enable Mutant Virus Attachment and Entry," *Journal of Virology*, 74(5):2481-2487 (Mar. 2000).

Asano et al., "Humanization of the Bispecific Epidermal Growth Factor Receptor X CD3 Diabody and Its Efficacy as a Potential Clinical Reagent," *Clin. Cancer Res.*, 12(13): 4036-4042 (Jul. 1, 2006).

Assi et al., "Gene Therapy for Brain Tumors: Basic Developments and Clinical Implementation," *Neurosci. Lett.*, 527(2): 71-77 (2012).

Baek et al., "Bispecific Adapter-Mediated Retargeting of a Receptor-Restricted HSV-1 Vector to CEA-Bearing Tumor Cells," *Molecular Therapy*, 19(3): 507-514 (Mar. 2011).

Bennett et al., "Comparison of safety, delivery, and efficacy of two oncolytic herpes viruses (G207 and NV1020) for peritoneal cancer," *Cancer Gene Therapy*, 9: 935-945 (2002).

Broberg et al., "Immune Response to Herpes Simplex Virus and $\gamma_1 34.5$ Deleted HSV Vectors," *Current Gene Therapy*, 5: 523-530 (2005).

Bzik et al., "Nucleotide Sequence of a Region of the Herpes Simplex Virus Type 1 gB Glycoprotein Gene: Mutations Affecting Rate of Virus Entry and Cell Fusion," *Virology*, 37:185-190 (1984).

Cai et al., "Linker-Insertion Nonsense and Restriction-Site Deletion Mutations of the gB Glycoprotein Gene of Herpes Simplex Virus Type 1," *Journal of Virology*, 67(3): 714-721 (Mar. 1987).

Camacho et al., "Phase 1 clinical trial of anti-CTLA4 human monoclonal antibody CP-675,206 in patients (pts) with advanced solid malignancies," *J. Clin. Oncol.*, 22(145): Abstract No. 2505 (2004) (antibody CP- 675206), 4 pp.

Campadelli-Fiume et al., "Rethinking herpes simplex virus: the way to oncolytic agents," *Rev. Med. Virol.*, 21: 213-226 (2011).

Cao et al., "A functional study of miR-124 in the developing neural tube," *Genes & Development*, 21: 531-536 (2007).

Cattaneo et al., "Reprogrammed viruses as cancer therapeutics: targets, armed and shielded," Nature Reviews. Microbiology, 6(7): 529-540 (2008).

Cawood et al., "Use of Tissue-Specific MicroRNA to Control Pathology of Wild-Type Adenovirus without Attenuation of Its Ability to Kill Cancer Cells," *PloS Pathogens*, 5(5): 1-10 (May 2009).

Cheadle et al., "Cloning and expression of the variable regions of mouse myeloma protein MOPC315 in *E. coli*: recovery of active $F_v$ fragments," *Mol. Immunol.*, 29(1): 21-30 (1992).

Cocchi et al., "The Ectodomain of a Novel Member of the Immunoglobulin Subfamily Related to the Poliovirus Receptor Has the Attributes of a Bona Fide Receptor for Herpes Simplex Virus Types 1 and 2 in Human Cells," *Journal of Virology*, 72(72): 9992-10002 (Dec. 1998).

Cocchi et al., "The Herpes Simplex Virus JMP Mutant Enters Receptor-Negative J Cells through a Novel Pathway Independent of the Known Receptors nectin1, HveA, and nectin2," *Journal of Virology*, 78(9): 4720-4729 (May 2004).

Conner et al., "A strategy for systemic delivery of the oncolytic herpes virus HSV1716: redirected tropism by antibody-binding sites incorporated on the virion surface as a glycoprotein D fusion protein," *Gene Therapy*, 15: 1579-1592 (2008).

Connolly et al., "Potential Nectin-1 Binding Site on Herpes Simplex Virus Glycoprotein D," *Journal of Virology*, 79(2): 1282-1295 (Jan. 2005).

Connolly et al., "Structure-Based Analysis of the Herpes Simplex Virus Glycoprotein D Binding Site Present on Herpevirus Entry Mediator HveA (HVEM)," *J. of Virology*, 76(21):10894-10904 (Nov. 2002).

Currier et al., "Efficacy and Safety of the Oncolytic Herpes Simplex Virus rRp450 Alone and Combined With Cyclophosphamide," *Molecular Therapy*, 16(5): 879-885 (2008).

Deluca et al., "Nucleotide Sequences of Herpes Simplex Virus Type 1 (HSV-1) Affecting Virus Entry, Cell Fusion, and Production of Glycoprotein gB (VP7)," *Virology*, 122: 411-423 (1982).

Desai et al., "Incorporation of the Green Fluorescent Protein into the Herpes Simplex Virus Type 1 Capsid," *Journal of Virology*, 72(9): 7563-7568 (Sep. 1998).

Dmitrieva et al., "Choindroitinase ABC I-mediated enhancement of oncolytic virus spread and anti tumor efficacy," *Clin. Cancer Res.*, 17(6): 1362-1372 (2011).

Doronina et al., "Site-Specific Release of Nascent Chains from Ribosomes at a Sense Codon," *Molecular and Cellular Biology*, 28(13): 4227-4239 (2008).

Edge et al., "A let-7 MicroRNA-sensitive Vesicular Stomatitis Virus Demonstrates Tumor-specific Replication," *Molecular Therapy*, 16(8): 1437-1443 (Aug. 2008).

Esko et al., "Animal Cell Mutants Defective in Glycosaminoglycan biosynthesis," *Proc. Natl. Acad. Sci. USA*, 82: 3197-3201 (May 1985).

Frampton et al., "Equine Herpesvirus 1 Enters Cells by Two Different Pathways, and Infection Requires the Activation of the Cellular Kinase ROCK1," *Journal of Virology*, 81(20): 10879-10889 (2007).

(56) References Cited

OTHER PUBLICATIONS

Friedman et al., "Herpes Simplex Virus Oncolytic Therapy for Pediatric Malignancies," *Molecular Therapy*, 17(7): 1125-1135 (2009).
Fu et al., "Construction of an Oncolytic Herpes Simplex Virus That Precisely Targets Hepatocellular Carcinoma Cells," *Mol. Ther.*, 20(2), 339-346 (2012).
Fujioka et al., "Interleukin-18 Protects Mice against Acute Herpes Simplex Virus Type 1 Infection," *J. of Virology*, 73(3): 2401-2409 (1999).
Fuller et al., "Anti-glycoprotein D Antibodies That Permit Adsorption but Block Infection by Herpes Simplex Virus 1 Prevent Virion-cell Fusion at the Cell Surface," *Proc. Natl. Acad. Sci. USA*, 84: 5454-5458 (Aug. 1987).
Fuller et al., "Neutralizing Antibodies Specific for Glycoprotein H of Herpes Simplex Virus Permit Viral Attachment to Cells but Prevent Penetration," *Journal of Virology*, 63(8): 3435-3443 (Aug. 1989).
Gaur et al., "Characterization of MicroRNA Expression Levels and Their Biological Correlates in Human Cancer Cell Lines," *Cancer Res.*, 67(6): 2456-2468 (2007).
Geraghty et al., "Entry of Alphaherpesviruses Mediated by Poliovirus Receptor-Related Protein 1 and Poliovirus Receptor," *Science*, 280: 1618-1620 (Jun. 5, 1998).
Gierasch et al., "Construction and Characterization of Bacterial Artificial Chromosomes Containing HSV-1 Strains 17 and KOS," *J. of Virological Methods*, 135: 197-206 (2006).
Grandi et al., "Design and application of oncolytic HSV vectors for glioblastoma therapy," *Expert Rev. Neurother.*, 9(4): 505-517 (2009).
Grossman et al., "Survival of Patients with Newly Diagnosed Glioblastoma Treated with Radiation and Temozolomide in Research Studies in the United States," *Clinical Cancer Research*, 16: 2443-2449 (2010).
Gubanova et al., "Onkoliticheskiye virusy v terapii gliom," *Molekulyamaya Biologiya (Mosk)*, 46(6), pp. 874-886 (Nov.-Dec. 2012), ISSN: 0026- 8984 (English abstract).
He et al., "Targeting Glioblastoma Stem Cells: Cell Surface Markers," *Current Medicinal Chemistry*, 19: 6050-6055 (2012).
Highlander et al., "Identification of mar Mutations in Herpes Simplex Virus Type 1 Glycoprotein B Which Alter Antigenic Structure and Function in Virus Penetration," *Journal of Virology*, 63(2): 730-738 (Feb. 1989).
Hodi et al., "Improved Survival with Ipilimumab in Patients with Metastatic Melanoma," *The New England Journal of Medicine*, 363(8): 711-723 (2010).
Hong et al., "Ectopic Matrix Metalloproteinase 9 Expression in Human Brain Tumor Cells Enhances Oncolytic HSV Vector Infection," *Gene Ther.*, 17(10): 1200-1205 (2010).
Iorio et al., "microRNA involvement in human cancer," *Carcinogenesis*, 33(6): 1126-1133 (2012).
Ishida et al., "Enhanced cytotoxicity with a novel system combining the paclitaxel-2'-ethylcarbonate prodrug and an HSV amplicon with an attenuated replication-competent virus, HF10 as a helper virus," *Cancer Letters*, 288: 17-27 (2010).
Jackson et al., "Insertion Mutations in Herpes Simplex Virus 1 Glycoprotein H Reduce Cell Surface Expression, Slow the Rate of Cell Fusion, or Abrogate Functions in Cell Fusion and Viral Entry," *Journal of Virology*, 84(4): 2038-2046 (Feb. 2010).
Kaji et al., "Virus free induction of pluripotency and subsequent excision of reprogramming factors," *Nature*, 458(7239): 771-775 (2009).
Kambara et al., "An Oncolytic HSV-1 Mutant Expressing ICP34.5 under Control of a Nestin Promoter Increases Survival of Animals even when Symptomatic from a Brain Tumor," *Cancer Res.*, 65(7): 2832-2839 (2005).
Karpowicz et al., "E-Cadherin Regulates Neural Stem Cell Self-Renewal," *The Journal of Neuroscience*, 29(12): 3885-3896 (2009).
Karsy et al., "Current Progress on Understanding MicroRNAs in Glioblastoma Multiforme," *Genes & Cancer*, 3(1): 3-15 (2012).
Katoh et al., "Hedgehog signaling, epithelial-to-mesenchymal transition and miRNA (Review)," *International Journal of Molecular Medicine*, 22: 271-275 (2008).
Košovský et al., "Herpes Simplex Virus 1 (HSV-1) Strain HSZP Glycoprotein B Gene: Comparison of Mutations among Strains Differing in Virulence," *Virus Genes*, 20(1): 27-33 (2000).
Krisky et al., "Rapid method for construction of recombinant HSV gene transfer vectors," *Gene Therapy*, 4: 1120-1125 (1997).
Krisky et al., "Deletion of multiple immediate-early genes from herpes simplex virus reduces cytotoxicity and permits long-term gene expression in neurons," *Gene Therapy*, 5: 1593-1603 (1998).
Krummenacher et al., "Effects of Herpes Simplex Virus on Structure and Function of Nectin-1/HveC," *Journal of Virology*, 76(5): 2424-2433 (Mar. 2002).
Kuan et al., "Increased Binding Affinity Enhances Targeting of Glioma Xenografts by EGFRVIII-Specific scFv," *Int. J. Cancer*, 88: 962-969 (2000).
Kumar et al., "Impaired microRNA processing enhances cellular transformation and tumorigenesis," *Nature Genetics*, 39(5): 673-677 (2007).
Kwon et al., "Soluble V Domain of Nectin-1/HveC Enables Entry of Herpes Simplex Virus Type 1 (HSV-1) into HSV-Resistant Cells by Binding to Viral Glycoprotein D," *Journal of Virology*, 80(1): 138-148 (Jan. 2006).
Lavon et al., "Gliomas display a microRNA expression profile reminiscent of neural precursor cells," *Neuro-Oncology*, 12(5): 422-433 (2010).
Lee et al., "MicroRNA Regulation of Oncolytic Herpes Simplex Virus-1 for Selective Killing of Prostate Cancer Cells," *Clin. Cancer Res.*, 15(16): 5126-5135 (Aug. 15, 2009).
Li et al., "Identification of Functional Domains in Herpes Simplex Virus 2 Glycoprotein B," *J. of Virology*, pp. 3792-3800 (Apr. 2006).
Ligas et al., "A Herpes Simplex Virus Mutant in Which Glycoprotein D Sequences Are Replaced by β-Galactosidase Sequences Binds to but is Unable to Penetrate into Cells," *J. of Virology*, 62(5): 1486-1494 (May 1988).
Lilley et al., "Multiple Immediate-Early Gene-Deficient Herpes Simplex Virus Vectors Allowing Efficient Gene Delivery to Neurons in Culture and Widespread Gene Delivery to the Central Nervous System In Vivo," *J. of Virology*, 75:9: 4343-4356 (May 2001).
Ma et al., "A novel HBV antisense RNA gene delivery system targeting hepatocellular carcinoma," *World J. of Gastro*, 9(3), 463-467 (2003).
MacDonald et al., "Genome Sequence of Herpes Simplex Virus 1 Strain KOS," *Journal of Virology*, 86(11): 6371-6372 (Jun. 2012).
McKee et al., "Degradation of Fibrillar Collagen in a Human Melanoma Xenograft improves the Efficacy of an Oncolytic Herpes Simplex Virus Vector," *Cancer Research*, 66(5): 2509-2513 (2006).
Mammoto et al., "Role of Collagen Matrix in Tumor Angiogenesis and Glioblastoma Multiforme Progression," *The American Journal of Pathology*, 183(4): 1293-1305 (2013).
Manickan et al., "Genetic immunization against herpes simplex virus. Protection is mediated by CD4+ T lymphocites," *The Journal of Immunology*, 155: 259-265 (1995).
Markert et al., "Conditionally replicating herpes simplex virus mutant, G207 for the treatment of malignant glioma: results of a phase I trial," *Gene Therapy*, 7: 867-874 (2000).
Mazzacurati et al., "Use of miRNA Response Sequences to Block Off-target Replication and Increase the Safety of an Unattenuated, Glioblastoma-targeted Oncolytic HSV," *Molecular Therapy*, 23(1): 99-107 (2015).
Menotti et al., "Construction of a Fully Retargeted Herpes Simplex Virus 1 Recombinant Capable of Entering Cells Solely via Human Epidermal Growth Factor Receptor 2," *Journal of Virology*, 82(20): 10153-10161 (Oct. 2008).
Menotti et al., "Inhibition of Human Tumor Growth in Mice by an Oncolytic Herpes Simplex Virus Designed to Target Solely HER-2-positive Cells," *PNAS*, 106(22): 9039-9044 (Jun. 2, 2009).
Miao et al., "Use of miRNA Response Sequences to Block Off-target Replication and Increase the Safety of an Unattenuated, Glioblastoma-targeted Oncolytic HSV," *Oncogene*, 34(5): 558-567 (2015).

(56) References Cited

OTHER PUBLICATIONS

Miest et al., "New viruses for cancer therapy: meeting clinical needs," *Nature Reviews. Microbiology*, 12(1): 23-34 (2014).
Miller et al., "Development of a Syngenic Murine B16 Cell Line-Derived Melanoma Susceptible to Destruction by Neuroattenuated HSV-1," *Molecular Therapy*, 3(2): 160-168 (Feb. 2001).
Milne et al., "Glycoprotein D Receptor-Dependent, Low-pH-Independent Endocytic Entry of Herpes Simplex Virus Type 1," *Journal of Virology*, 79(11): 6655-6663 (Jun. 2005).
Mohyeldin et al., "Gene and Viral Therapy for Glioblastoma A Review of Clinical Trials and Future Directions," *The Cancer Journal*, 18(1): 82-88 (2012).
Mok et al., "Matrix Metalloproteinases-1 and -8 Improve the Distribution and Efficacy of an Oncolytic Virus," *Cancer Res.*, 67(22): 10664-10668 (2007).
Montgomery et al., "Herpes Simplex Virus-1 Entry into Cells Mediated by a Novel Member of the TNF/NGF Receptor Family," *Cell*, 87: 427-436 (Nov. 1, 1996).
Muggeridge, "Characterization of Cell-cell Fusion Mediated by Herpes Simplex Virus 2 glycoproteins gB, gD, gH and gL in Transfected Cells," *Journal of General Virology*, 81:2017-2027 (2000).
Mullokandov et al. "High-throughput assessment of microRNA activity and function using microRNA sensor and decoy libraries," *Nature Methods*, 9, pp. 840-846 (2012).
Nakano et al., "Mechanism of HSV infection through soluble adapter-mediated virus bridging to the EGF receptor," *Virology*, 413: 12-18 (2011).
Navaratnarajah et al., "Targeted Entry of Enveloped Viruses: Measles and Herpes Simplex Virus I," *Curr. Opin. Virol.*, 2(1): 43-49 (2012).
NCBI, "Human Herpesvirus 1 Strain KOS Glycoprotein B Gene," Database GenBank Accession No. AF311740 (Jan. 24, 2001), retrieved Oct. 15, 2012.
NCBI, "Herpes Simplex Virus Type 1 Gene for Glycoprotein gH," Database GenBank Accession No. X03896 (Apr. 18, 2005), retrieved Oct. 15, 2012.
NCBI, "Human Herpesvirus 1 Complete Genome," Databse GenBank Accession No. X14112 (Oct. 23, 2008), retrieved Oct. 15, 2012.
NCBI, "glycoprotein B [Human herpesvirus 1]," Database Entrez-Nucleotide, Accession No. AAF70301 (May 16, 2000), retrieved May 19, 2015.
NCBI, "glycoprotein B [Human herpesvirus 1]," Database Entrez-Nucleotide, Accession No. AAA91805 (Mar. 8, 1996), retrieved May 19, 2015.
NCBI, "Chain A, Glycoprotein B From Herpes Simplex Virus Type 1, A549t Rate-of-entry Mutant, Low-ph," Database Entrez-Nucleotide, Accession No. 4L1R_A (Jun. 26, 2013), retrieved May 19, 2015.
Nduom et al., "Glioblastoma Cancer Stem-like Cells—Implications for Pathogenesis and Treatment," *Cancer J.*, 18(1): 100-106 (2012).
Nicola et al., "Roles for Endocytosis and Low pH in Herpes Simplex Virus Entry into HeLa and Chinese Hamster Ovary Cells," *Journal of Virology*, 77(9): 5324-5332 (May 2003).
Nicola et al., "Cellular and Viral Requirements for Rapid Endocytic Entry of Herpes Simplex Virus," *Journal of Virology*, 78(14): 7508-7517 (Jul. 2004).
Ocana et al., "A new regulatory loop in cancer-cell invasion," *European Molecular Biology Organization*, 9(6): 521-522 (2008).
Omidfar et al., "Production of a Novel Camel Single-Domain Antibody Specific for the Type III Mutant EGFR," *Tumor Biology*, 25: 296-305 (2004).
Omidfar et al., "Production and Characterization of a New Antibody Specific for the Mutant EGF Receptor, EGFRvIII, in Camelus bactrianus," *Tumor Biology*, 25:179-187 (2004).
Opalinska et al., "Nucleic-Acid Therapeutics: Basic Principles and Recent Applications," *Nature Reviews*, 1, pp. 503-514 (2002).
Parker et al., "Oncolytic Viral Therapy of Malignant Glioma," *Neurotherapeutics: The Journal of the American Society for Experimental NeuroTherapeutics*, 6: 558-569 (2009).
Patriarca et al., "Epithelial cell adhesion molecule expression (CD326) in cancer: A short review," *Cancer Treatment Reviews*, 38: 68-75 (2012).
Payne et al., "The Pathobiology of Collagens in Glioma," *Mol. Cancer Res.*, 11: 1129-1140 (2013).
Pertel et al., "Cell Fusion Induced by Herpes Simplex Virus Glycoproteins gB, gD, and gH-gL Requires a gD Receptor but Not Necessarily Heparan Sulfate," *Virology*, 279: 313-324 (2001).
Raag et al., "Single-chain Fvs," *FASEB*, 9(1):73-80 (1995).
Rauch et al., "Mutations in Herpes Simplex Virus Glycoprotein D Distinguish Entry of Free Virus from Cell-Cell Spread," *Journal of Virology*, 74(24): 11437-11446 (Dec. 2000).
Riddick et al., "Integration and analysis of genome-scale data from gliomas," *Nature Reviews—Neurology*, 7: 439-450 (2011).
Saharkhiz-Langroodi et al., "Identification of the Fusion-from-without Determinants of Herpes Simplex Virus Type 1 Glycoprotein B," *Virology*, 227, 153-159 (1997).
Schaffer et al., "Temperature-Sensitive Mutants of Herpes Simplex Virus Type 1: Isolation, Complementation and Partial Characterization," *Virology*, 52: 57-71 (1973).
Sethi et al., "Protection of Mice from Fatal Herpes Simplex Virus Type 1 Infection by Adoptive Transfer of Cloned Virus-specific and H-2-restricted Cytotoxic T Lymphocytes," *J. Gen. Virol.*, 64: 443-447 (1983).
Shogan et al., "Virucidal Activity of a GT-Rich Oligonucleotide against Herpes Simplex Virus Mediated by Glycoprotein B," *Journal of Virology*, 80(10): 4740-4747 (May 2006).
Shi et al., "hsa-mir-181a and hsa-mir-181b function as tumor suppressors in human glioma cells," *Brain Research*, 1236: 185-193 (2008).
Silber et al., "miR-124 and miR-137 inhibit proliferation of glioblastoma multiforme cells and induce differentiation of brain tumor stem cells," *BMC Medicine*, 6(14): 1-17 (2008).
Slavuljica et al., "Recombinant mouse cytomegalovirus expressing a ligand for the NKG2d receptor is attenuated and has improved vaccine properties," *J. Clin. Invest.*, 120(12): 4532-4545 (Dec. 2010).
Smith, "Relationship Between the Envelope and the Infectivity of Herpes Simplex Virus," *Herpes Virus Envelopes*, 814-816 (1964).
Struyf et al., "Mutations in the N-Terminal Domains of Nectin-1 and Nectin-2 Reveal Differences in Requirements for Entry of Various Alphaherpesviruses and for Nectin-Nectin Interactions," *Journal of Virology*, 76(24): 12940-12950 (Dec. 2002).
Szymczak et al., "Development of 2A peptide-based strategies in the design of multicistronic vectors," *Expert Opin. Biol. Ther.*, 5(5): 627-638 (2005).
Thomas et al., "Equine Herpesvirus 1 Gene 12 Can Substitute for vmw65 in the Growth of Herpes Simplex Virus (HSV) Type 1, Allowing the Generation of Optimized Cell Lines for the Propagation of HSV Vectors with Multiple Immediate-Early Gene Defects," *J. of Virology*, 73(9): 7399-7409 (Sep. 1999).
Tischer et al., "Two-step Red-mediated recombination for versatile high-efficiency markerless DNA manipulation in *Escherichia coli*," *BioTechniques*, 40(2): 191-196 (2006).
Todo, "Oncolytic Virus Therapy Using Genetically Engineered Herpes Simplex Viruses," *Human Cell*, 15(3): 151-159 (2002).
Topalian et al., "Safety, Activity, and Immune Correlates of Anti-PD-1 Antibody in Cancer," *The New England Journal of Medicine*, 366(26): 2443-2454 (2012).
Tsvitov et al., "Characterization of Soluble Glycoprotein D-mediated Herpes Simplex Virus Type 1 Infection," *Virology*, 360: 477-491 (2007).
Turner et al., "Glycoproteins gB, gD, and gHgL of Herpes Simplex Virus Type 1 Are Necessary and Sufficient to Mediate Membrane Fusion in a Cos Cell Transfection System," *Journal of Virology*, 72(1): 873-875 (Jan. 1998).
Uchida et al., "Effective Treatment of an Orthotopic Xenograft Model of Human Glioblastoma Using an EGFR-retargeted Oncolytic Herpes Simplex Virus," *Molecular Therapy*, 21(3): 561-569 (2013).
Uchida et al., "Hyperactive Glycoprotein B (gB) Mutations Augment Fully Retargeted Herpes Simplex Virus (HSV) Infection,"

(56) References Cited

OTHER PUBLICATIONS

*101st Annual Meeting of the American Association for Cancer Research*, poster presentation, 1 page, Washington, DC (Apr. 18, 2010).
Uchida et al., "Identification of Mutations in HSV-1 Envelope Glycoprotein B That Enhance Retargeted Infection," *Proceedings of the American Association for Cancer Research*, 51: 139, Abstract 584 (Apr. 2010).
Uchida et al., "Hyperactive gB Mutations Augment Fully Retargeted HSV Infection," *13th Annual Meeting of the American Society of Gene & Cell Therapy*, slides of oral presentation, 34 pages, Washington, DC (May 19-22, 2010).
Uchida et al., "Fully Retargeted HSV-1 Infection Directed by Re-Engineered Glycoprotein D (gD) is Augmented by Hyperactive gB Mutations," *Molecular Therapy*, 18(Supp. 1): S249, Abstract 640 (May 2010).
Uchida et al., "Co-engineering of HSV-1 GB and gD Enables Efficient Retargeted Infection," *29th Annual Meeting of the American Society for Virology*, slides of oral presentation, 38 pages, Bozeman, MT (Jul. 17-21, 2010).
Uchida et al., "Co-engineering of HSV-1 Glycoproteins B and D Enables Highly Efficient Retargeted Infection," *29th Annual Meeting of the American Society for Virology*, abstract, 1 page, Bozeman, MT (Jul. 17-21, 2010).
Uchida et al., "Hyperactive gB Mutations Augment Fully Retargeted HSV Infection," *35th Annual International Herpes Virus Workshop*, poster presentation, 1 page, Salt Lake City, UT (Jul. 24-29, 2010).
Uchida et al., "Hyperactive Glycoprotein B Mutations Augment Fully Retargeted HSV Infection," *35th Annual International Herpes Virus Workshop*, abstract, 1 page, Salt Lake City, UT (Jul. 24-29, 2010).
Uchida et al., "A Double Mutation in Glycoprotein gB Compensates for Ineffective gD-Dependent Initiation of Herpes Simplex Virus Type 1 Infection," *Journal of Virology*, 84(23): 12200-12209 (Dec. 2010).
Uchida et al., "Generation of Herpesvirus Entry Mediator (HVEM)—Restricted Herpes Simplex Virus Type 1 Mutant Viruses: Resistance of HVEM-Expressing Cells and Identification of Mutations That Rescue Nectin-1 Recognition," *Journal of Virology*, 83(7): 2951-2961 (Apr. 2009).
Uchida et al., "Novel Mutations in gB and gH Circumvent the Requirement for Known gD Receptors in Herpes Simplex Virus 1 Entry and Cell-to-Cell Spread," *Journal of Virology*, 87(3): 1430-1442 (Feb. 2013).
Ushijima et al., "Determination and Analysis of the DNA Sequence of Highly Attenuated Herpes Simplex Virus Type 1 Mutant HF10, a Potential Oncolytic Virus," *Microbes and Infection*, 9: 142-149 (2007).
Varghese et al., "Oncolytic herpes simplex virus vectors for cancer virotherapy," *Cancer Gene Therapy*, 9(12): 967-978 (2002).
Verhaak et al., "Integrated Genomic Analysis Identifies Clinically Relevant Subtypes of Glioblastoma Characterized by Abnormalities in PDGFRA, IDH1, EGFR, and NF1," *Cancer Cell*, 17: 98-110 (2010).
Visvanathan et al., "The microRNA miR-124 antagonizes the anti-neural REST/SCP1 pathway during embryonic CNS development," *Genes & Development*, 21: 744-749 (2007).
Voeks et al., "Gene therapy for prostate cancer delivered by ovine adenovirus and mediated by purine nucleoside phosphorylase and fludarabine in mouse models," *Gene Therapy*, 9(12): 759-768 (2002).
Wakimoto et al., "Effects of innate immunity on herpes simplex virus and its ability to kill tumor cells," *Gene Therapy*, 10: 983-990 (2003).
Warner et al., "A Cell Surface Protein with Herpesvirus Entry Activity (HveB) Confers Susceptibility to Infection by Mutants of Herpes Simplex Virus Type 1, Herpes Simples Virus Type 2, and Pseudorabies Virus," *Virology*, 246: 179-189 (1998).
Wikstrand et al., "Monoclonal Antibodies against EGFRvIII Are Tumor Specific and React with Breast and Lung Carcinomas and Malignant Gliomas," Cancer Research, 55: 3140-3148 (Jul. 15, 1995).
Wong et al., "Targeted Oncolytic Herpes Simplex Viruses for Aggressive Cancers," *Current Pharmaceutical Biotechnology*, 13: 1786-1794 (2012).
Xia et al., "Loss of Brain-enriched miR-124 MicroRNA Enhances Stem-like Traits and Invasiveness of Glioma Cells," *The Journal of Biological Chemistry*, 287(13): 9962-9971 (2012).
Yan et al., "Effective small RNA destruction by the expression of a short tandem target mimic in Arabidopsis," *The Plant Cell*, 24, pp. 415-427 (2012).
Yin et al., "The treatment of glioblastomas: A systematic update on clinical Phase III Trials," *Critical Reviews in Oncology/Hematology*, 87: 265-282 (2013).
Yun, "Overcoming the extracellular matrix barrier to improve intratumoral spread and therapeutic potential of oncolytic virotherapy," *Current Opinion in Molecular Therapeutics*, 10(4): 356-361 (2008).
Zhang et al., "MicroRNA-128 inhibits glioma cells proliferation by targeting transcription factor E2F3a," *J. Mol. Med.*, 87: 43-51 (2009).
Zhang et al., "Abstract 3669: IDH mutant glial cell resistance to natural killer cell cytotoxicity," *Cancer Research*, 74, 3669 (Oct. 1, 2014).
Zhou et al., "Construction and Properties of a Herpes Simplex Virus 1 Designed to Enter Cells Solely via the IL-13α2 Receptor," *PNAS*, 103(14): 5508-5513 (Apr. 4, 2006).

\* cited by examiner

```
                         SEQUENCE LISTING

<160> NUMBER OF SEQ ID NOS: 10

<210> SEQ ID NO 1
<211> LENGTH: 9
<212> TYPE: PRT
<213> ORGANISM: Artificial Sequence
<220> FEATURE:
<223> OTHER INFORMATION: gB:D285
<220> FEATURE:
<221> NAME/KEY: MISC_FEATURE
<222> LOCATION: (5)..(5)
<223> OTHER INFORMATION: wherein Xaa is other than D

<400> SEQUENCE: 1

Val Tyr Pro Tyr Xaa Glu Phe Val Leu
1               5

<210> SEQ ID NO 2
<211> LENGTH: 9
<212> TYPE: PRT
<213> ORGANISM: Artificial Sequence
<220> FEATURE:
<223> OTHER INFORMATION: gB:A549
<220> FEATURE:
<221> NAME/KEY: MISC_FEATURE
<222> LOCATION: (6)..(6)
<223> OTHER INFORMATION: wherein Xaa is other than A

<400> SEQUENCE: 2

Lys Leu Asn Pro Asn Xaa Ile Ala Ser
1               5

<210> SEQ ID NO 3
<211> LENGTH: 9
<212> TYPE: PRT
<213> ORGANISM: Artificial Sequence
<220> FEATURE:
<223> OTHER INFORMATION: gB:S668
<220> FEATURE:
<221> NAME/KEY: MISC_FEATURE
<222> LOCATION: (5)..(5)
<223> OTHER INFORMATION: wherein Xaa is other than S

<400> SEQUENCE: 3

Ile Thr Thr Val Xaa Thr Phe Ile Asp
1               5

<210> SEQ ID NO 4
<211> LENGTH: 9
<212> TYPE: PRT
```

<213> ORGANISM: Artificial Sequence
<220> FEATURE:
<223> OTHER INFORMATION: gH:N753
<220> FEATURE:
<221> NAME/KEY: MISC_FEATURE
<222> LOCATION: (5)..(5)
<223> OTHER INFORMATION: wherein Xaa is other than N

<400> SEQUENCE: 4

Val Asp Thr Asp Xaa Thr Gln Gln Gln
1               5

<210> SEQ ID NO 5
<211> LENGTH: 9
<212> TYPE: PRT
<213> ORGANISM: Artificial Sequence
<220> FEATURE:
<223> OTHER INFORMATION: gH:A778
<220> FEATURE:
<221> NAME/KEY: MISC_FEATURE
<222> LOCATION: (5)..(5)
<223> OTHER INFORMATION: wherein Xaa is other than A

<400> SEQUENCE: 5

Val Pro Ser Thr Xaa Leu Leu Leu Phe
1               5

<210> SEQ ID NO 6
<211> LENGTH: 9
<212> TYPE: PRT
<213> ORGANISM: Artificial Sequence
<220> FEATURE:
<223> OTHER INFORMATION: gB:D285N

<400> SEQUENCE: 6

Val Tyr Pro Tyr Asn Glu Phe Val Leu
1               5

<210> SEQ ID NO 7
<211> LENGTH: 9
<212> TYPE: PRT
<213> ORGANISM: Artificial Sequence
<220> FEATURE:
<223> OTHER INFORMATION: gB:A549T

<400> SEQUENCE: 7

Lys Leu Asn Pro Asn Thr Ile Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: gB:S668N

<400> SEQUENCE: 8

Ile Thr Thr Val Asn Thr Phe Ile Asp
1               5

<210> SEQ ID NO 9
<211> LENGTH: 9
<212> TYPE: PRT
<213> ORGANISM: Artificial Sequence
<220> FEATURE:
<223> OTHER INFORMATION: g

```
Val Asp Thr Asp Lys Thr Gln Gln Gln
1               5

<210> SEQ ID NO 10
<211> LENGTH: 9
<212> TYPE: PRT
<213> ORGANISM: Artificial Sequence
<220> FEATURE:
<223> OTHER INFORMATION: gH:A778V

<400> SEQUENCE: 10

Val Pro Ser Thr Val Leu Leu Leu Phe
1               5
```

IDENTIFICATION OF MUTATIONS IN HERPES SIMPLEX VIRUS ENVELOPE GLYCOPROTEINS THAT ENABLE OR ENHANCE VECTOR RETARGETING TO NOVEL NON-HSV RECEPTORS

CROSS-REFERENCE TO RELATED APPLICATIONS

This patent application is a continuation of U.S. patent application Ser. No. 15/409,245, filed Jan. 18, 2017, now U.S. Pat. No. 10,328,136, which is a continuation of U.S. patent application Ser. No. 15/137,953, filed Apr. 25, 2016, now abandoned, which is a continuation of U.S. patent application Ser. No. 13/641,649, filed Dec. 28, 2012, now U.S. Pat. No. 9,593,347, which is a U.S. National Phase of International Patent Application PCT/US2011/032923, filed Apr. 18, 2011, which claims the benefit of U.S. Provisional Patent Application 61/325,137, filed Apr. 16, 2010, each of which is incorporated by reference.

STATEMENT REGARDING FEDERALLY SPONSORED RESEARCH AND DEVELOPMENT

This invention was made with Government support under Grant Numbers CA119298, NS40923, and DK044935 awarded by the National Institutes of Health. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,898 Byte ASCII [Text] file named 739052_ST25.TXT created on Jan. 31, 2020.

BACKGROUND OF THE INVENTION

In recent years, the potential of viral vectors or genetically engineered viruses for the treatment of a variety of human diseases has been a topic of intense study worldwide. Herpes simplex virus (HSV) is among the most promising platforms for these purposes because of its efficient entry and spread into a wide range of cell types and its ability to accommodate expression cassettes for multiple or very large foreign genes that can provide therapeutic functions.

Targeting of HSV infection to specific cells for the delivery of therapeutic products or lytic infection of cancer cells requires (i) elimination of the native ability of the virus to interact with its entry receptors, mainly nectin-1 and HVEM, and (ii) the availability of a mechanism to trigger the virus entry process in response to virus engagement of alternate receptors. The attachment and fusion steps of HSV infection are mediated primarily by components of the viral envelope, a membranous structure containing at least 10 glycoproteins (gB, gC, gD, gE, gG, gH, gI, gJ, gL, and gM) and four non-glycosylated integral membrane proteins (UL20, UL34, UL45, and UL49.5). Of the glycoproteins, gB, gD, gH, and gL are essential for wild type herpes viruses to infect their host cells, while the remainder are dispensable for viral attachment or internalization. Prior to HSV-1 entry, virions are adsorbed to the cell surface through binding of gC and gB, to exposed glycosaminoglycans on the cell membrane. The entry process is then initiated by the interaction of gD with one of its cognate receptors, such as herpesvirus entry mediator (HVEM) or nectin-1. Receptor binding results in a conformational change in gD triggering activation of gB and a fourth envelope glycoprotein, gH, as the effectors of fusion between the viral envelope and cell membranes.

The virus can also infect cells by moving transcellularly, (e. g., at the sites of gap junctions), a process referred to as lateral spread. The process of lateral spread to neighboring cells also involves the envelope proteins; however different proteins appear to be essential for each process. Thus, for example, while gE, and gI are not essential for primary infection at the cell surface, removal of either of these greatly inhibits lateral spread.

Based on this understanding of the HSV-1 cell attachment and entry process, gC and gD have been modified to eliminate recognition of their natural receptors ("detargeting") and insert a targeting element to provide a novel interaction with specific receptors on the target cell ("retargeting"). Although these approaches have shown promising results in terms of ablation of virus entry through the natural receptors, the efficiency of retargeted entry has not been universally high, thus limiting the practical application of these vectors. In fact, there has been only one example in the literature of efficient HSV-1 retargeting (Menotti et al., *J. Virol.*, 82(20), 10153-61 (2008); Menotti et al., *PNAS USA*, 106(22) 9039-44 (2009)), and some attempts to take advantage of this design (replacement of residues 61-218 of gD with a single-chain antibody [scFv] against HER-2) to target the EGF receptor (EGFR) using an EGFR-specific scFv, have been unsuccessful.

It is clear, therefore, that a methodology is needed to enhance retargeted virus entry and spread, as such can reduce the effective virus dose and thereby increase safety.

BRIEF SUMMARY OF THE INVENTION

The invention provides modified HSV vectors that exhibit enhanced entry of cells, either through direct infection and/or lateral spread. In one aspect, HSV vectors of the present invention can directly infect cells through interaction with cell proteins other than typical mediators of HSV infection (e.g., other than nectin-1, HVEM, heparan sulfate/chondroitin sulfate proteoglycans. In another aspect, the invention provides an HSV vector, such as comprising mutant gH glycoproteins, which HSV vector exhibits lateral spread in cells typically resistant to HSV lateral spread, such as cells lacking gD receptors.

In yet another aspect, the invention provides an HSV vector comprising an envelope having one or more mutant envelope proteins, whereby said HSV vector exhibits at least 25% increased rate-of-entry after 20 minutes when assayed at either 30° C. or 37° C. in Vero cells after first incubating at 4° C. relative to an HSV comprising a wild-type gB and/or gH protein.

In another aspect, the invention provides an HSV vector comprising a mutant gB and/or a mutant gH glycoprotein, wherein the HSV comprises mutations at two or more of group of residues consisting of gB:D285, gB:A549, gB:S668, gH:N753, and gH:A778, wherein said mutations are relative to the sequence of HSV-1 strain KOS derivative K26GFP or GenBank Accession No. AF311740 or GenBank Accession No. X03896.

In a further aspect, the invention provides an HSV vector comprising an envelope having one or more mutant envelope proteins other than gD or gC, whereby said HSV vector infects a cell via interaction of gD and/or gC with a cell surface protein other than or in addition to known gD or gC receptors such as nectin-1, HVEM, and heparan sulfate/chondroitin sulfate proteoglycans.

In still another aspect, the invention provides a viral stock comprising an HSV vector as described herein.

In another aspect, the invention provides a DNA molecule encoding an HSV vector as described herein. In particular, the invention provides a DNA molecule comprising a sequence of nucleic acids encoding a mutant gB glycoprotein having a mutation at one or more of the following residues: gB:D285, gB:A549, and/or gB:S668, wherein the mutation in gB is relative to the sequence of HSV-1 strain KOS derivative K26GFP or GenBank Accession No. AF311740, as well as a DNA molecule comprising a sequence of nucleic acids encoding a mutant gH glycoprotein having a mutation at one or more of the following residues: gH:N753 and/or gH:A778, wherein the mutation in gH is relative to the sequence of HSV-1 strain KOS derivative K26GFP or GenBank Accession No. X03896.

The invention provides a method of increasing the efficiency of viral entry of a retargeted HSV vector comprising (a) retargeting the HSV vector by mutating a gC and/or gD envelope glycoprotein to comprise a non-native ligand specific for a cell surface receptor, and (b) mutating an envelope glycoprotein other than gD such that the resulting vector can enter a cell via the interaction between said non-native ligand and the cell surface receptor at least 10 times more efficiently than a control HSV vector comprising the non-native ligand of (a) but lacking the mutated envelope glycoprotein of (b). Optionally, the gC and/or gD envelope glycoprotein is impaired for binding to its natural receptor or is deleted.

In another aspect, the invention provides a method of killing a cancer cell comprising contacting the cancer cell with an HSV vector as described herein.

BRIEF DESCRIPTION OF THE SEVERAL VIEWS OF THE DRAWING(S)

FIG. 1 depicts plaque-forming activities per viral genome for isolates 1-4, parent virus K26-gD:2/3NI, and control K26GFP on B78H1 cells and derivatives expressing intact HSV entry receptors (HVEM, B78/A; nectin-1, B78/C) or a debilitated receptor (mutant nectin-1, B78/TMC). Biological titers of the virus stocks in pfu/ml were determined on each cell line by standard procedures. Genome titers of the stocks in gc (genome copies)/ml were determined by qPCR for the viral ICP47 gene. Biological titers were divided by genome titers and the mean values±SD from 3 determinations plotted on a logarithmic scale. *, <10-7.

Figure 2A:
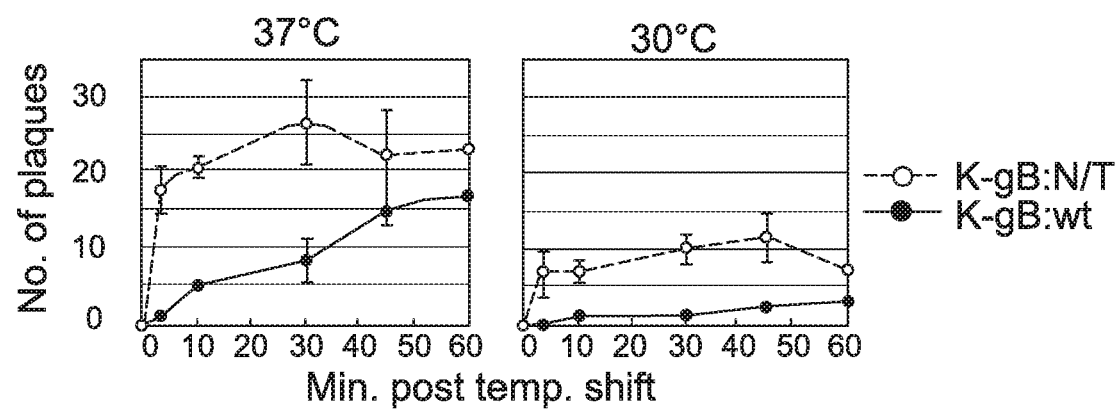

FIG. 2A is a time course of virus entry into B78/C cells. Cells were incubated with 200 pfu of K-gB:wt or K-gB:N/T at 4° C. for 30 min, washed thoroughly, incubated at 37 or 30° C. for the indicated times, and treated with acidic buffer. Cells were then incubated at 37° C. under methylcellulose-containing media for 3 days to allow plaque formation. Plaques were counted and the mean values±SD from 3 determinations plotted.

Figure 2B:
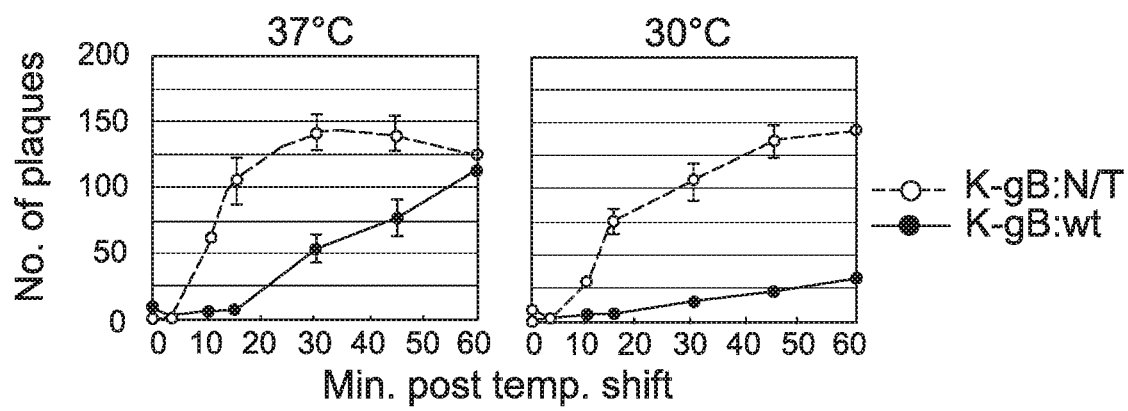

FIG. 2B is a time course of virus entry into Vero cells. Cells were incubated with 200 pfu of K-gB:wt or K-gB:N/T at 4° C. for 30 min, washed thoroughly, incubated at 37 or 30° C. for the indicated times, and treated with acidic buffer. Cells were then incubated at 37° C. under methylcellulose-containing media for 3 days to allow plaque formation. Plaques were counted and the mean values±SD from 3 determinations plotted.

Figure 3A:
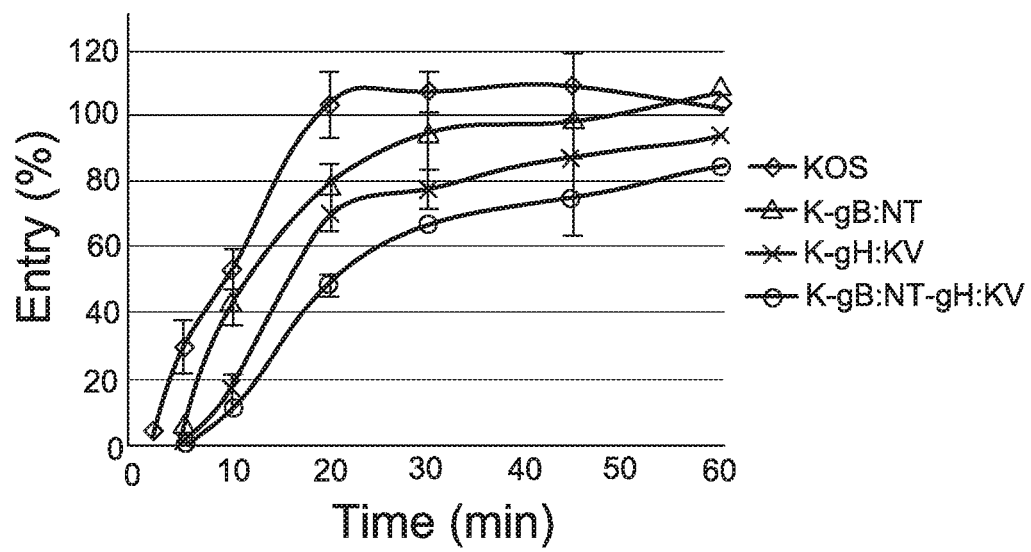
Figure 3B:
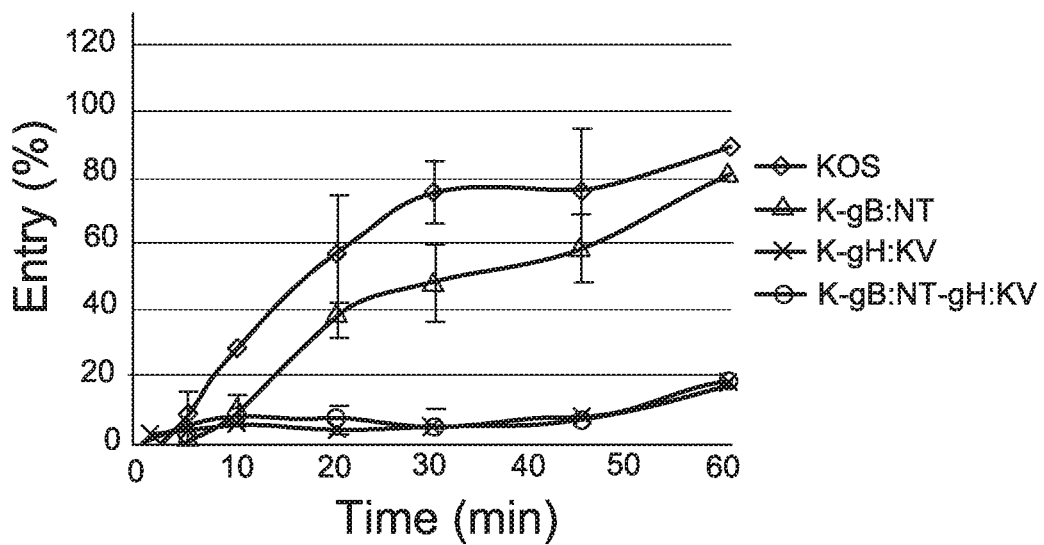

FIG. 3A and FIG. 3B is a time course of virus entry into Vero cells comparing wild-type HSV-1 KOS with derivatives containing a mutant gB (gB:N/T) and/or gH allele (gH:N753K/A778V). Cells were incubated with 500 pfu of each virus at 4° C. for 30 min, washed thoroughly, incubated at (FIG. 3A) 37° C. or (FIG. 3B) 30° C. for the indicated times, and treated with acidic buffer. Cells were then incubated at 37° C. under methylcellulose-containing media for 2 days to allow plaque formation. Plaque numbers were counted and divided by the number of plaques formed by the same virus incubated for 2 h at 37° C. without acid treatment to calculate % entry. Mean values±SD from triplicate samples were plotted.

Figure 4A:
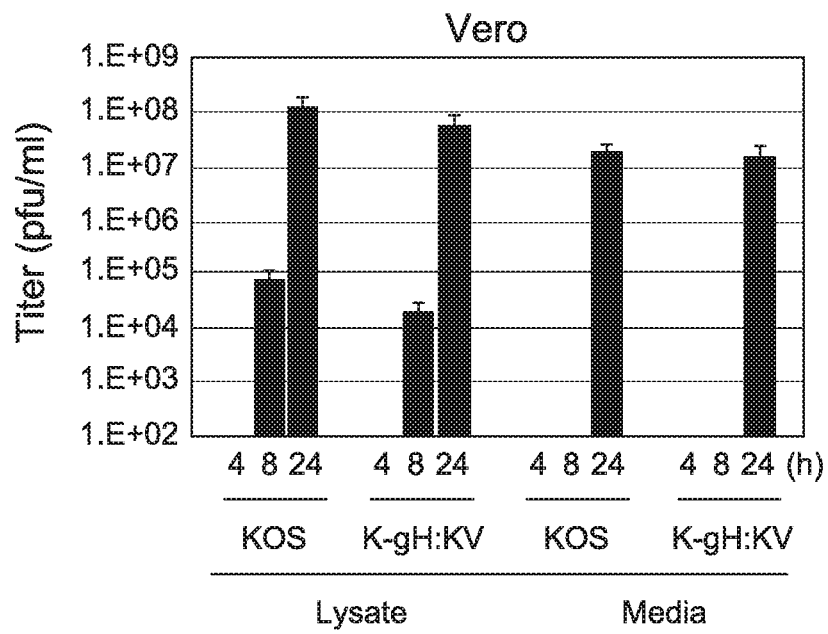

FIG. 4A depicts virus yields over time in lysates versus media for Vero cells infected at an MOI of 3 for 1 h followed by acid treatment and incubation at 37° C. with fresh media. Cell lysates and media were collected at 4, 8, and 24 h post-infection (pi) and titered on Vero cells. Viruses were wild-type HSV-1 KOS and derivative K-gH:KV carrying the gH:N753K/A778V mutant allele.

Figure 4B:
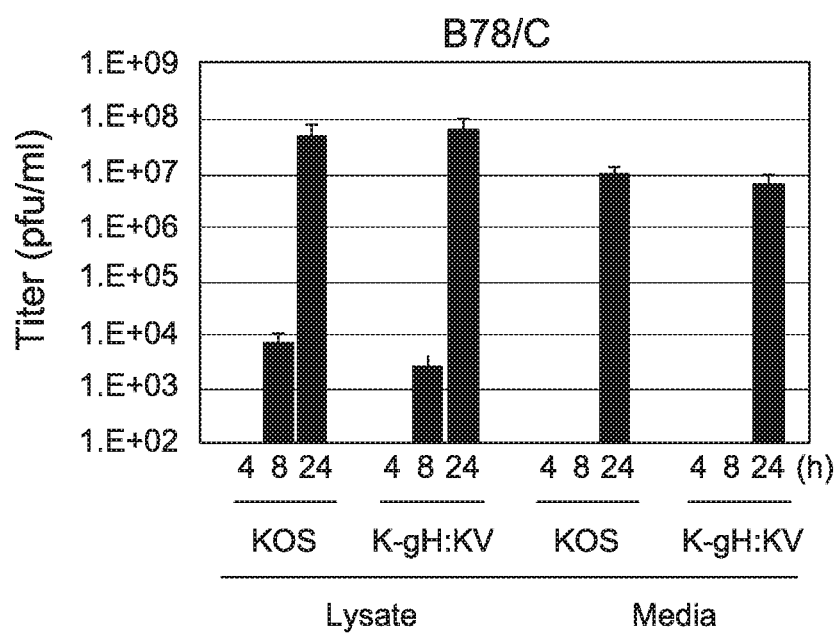

FIG. 4B depicts virus yields over time in lysates versus media for B78/C cells infected at an MOI of 3 for 1 h followed by acid treatment and incubation at 37° C. with fresh media. Cell lysates and media were collected at 4, 8, and 24 h post-infection (pi) and titered on Vero cells. Viruses were wild-type HSV-1 KOS and derivative K-gH:KV carrying the gH:N753K/A778V mutant allele.

Figure 5:
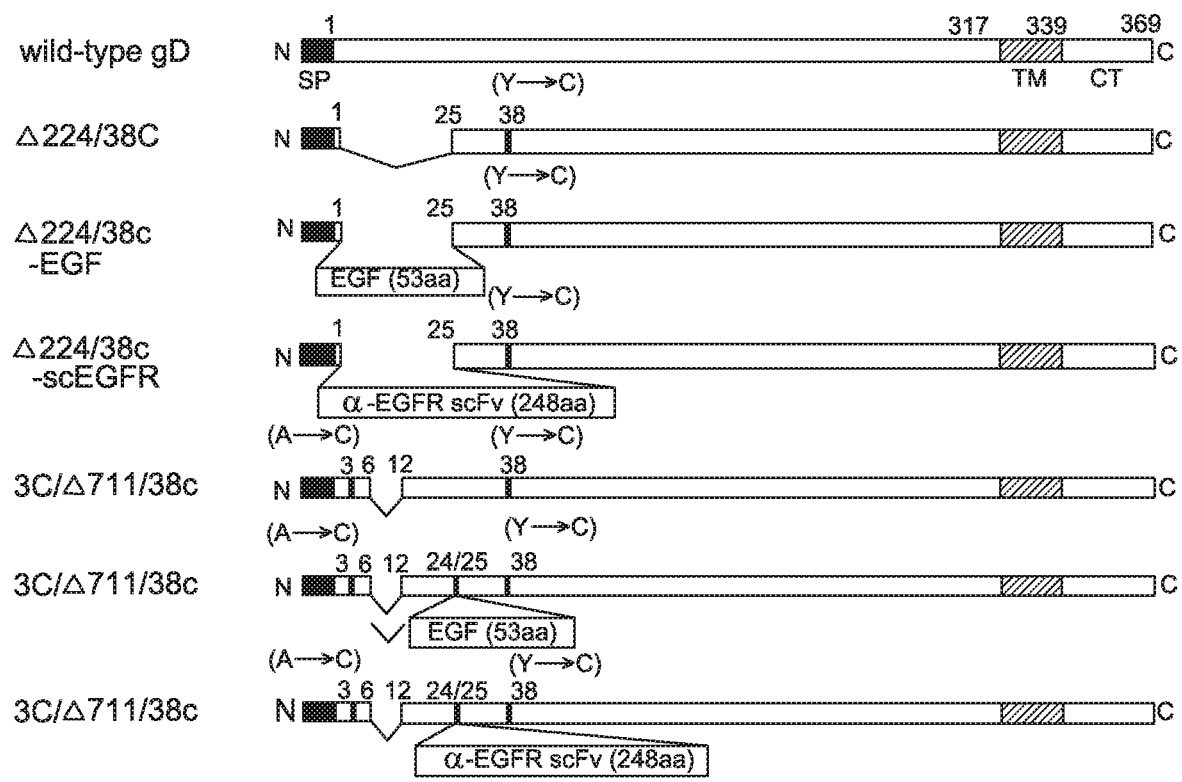

FIG. 5 provides schematic representation of detargeted and retargeted gD-mutant constructs. Abbreviations: SP, signal peptide; TM, transmembrane domain; CT, cytoplasmic tail; aa, amino acids.

Figure 6:
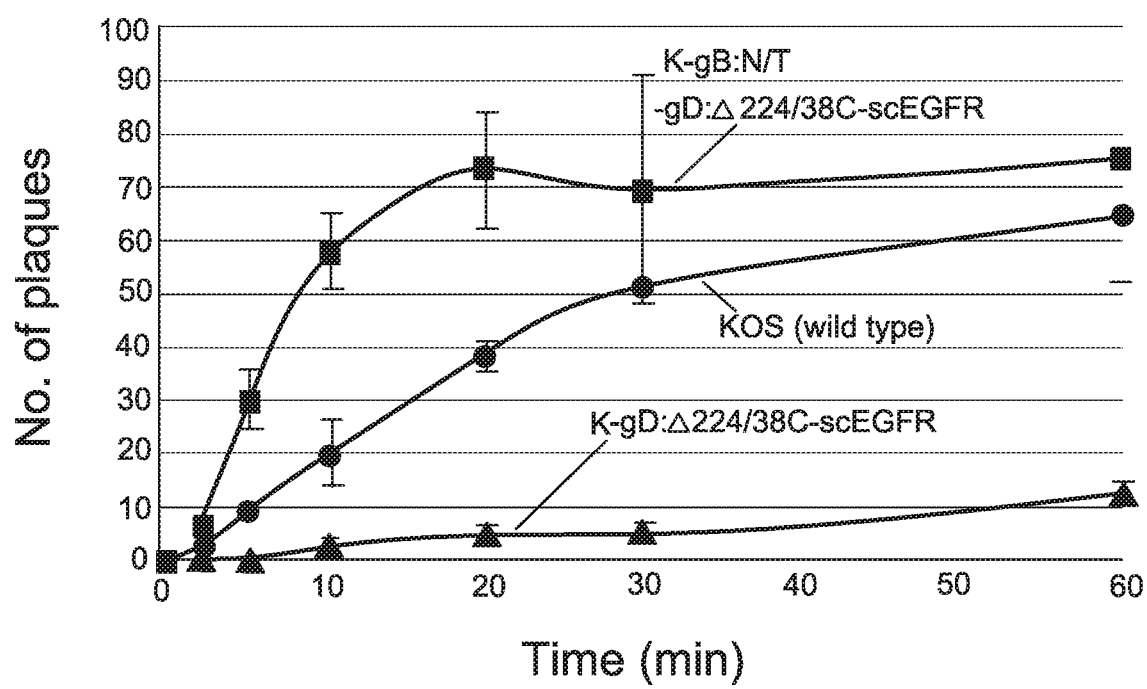

FIG. 6 depicts a time course of virus entry into gD-complementing Vero cells (VD60) as measured by plaque formation at 2 dpi. Cells were incubated with 20,000 gc of wild-type KOS, K-gD:Δ224/38C-scEGFR, or K-gB:N/T-gD:Δ224/38C-scEGFR at 4° C. for 30 min, washed thoroughly, incubated at 37° C. for the indicated times, and treated with acidic buffer. Cells were then incubated at 37° C. under methylcellulose-containing media for 2 days to allow plaque formation. Plaques were counted and the mean values±SD from 3 determinations plotted.

Figure 7:
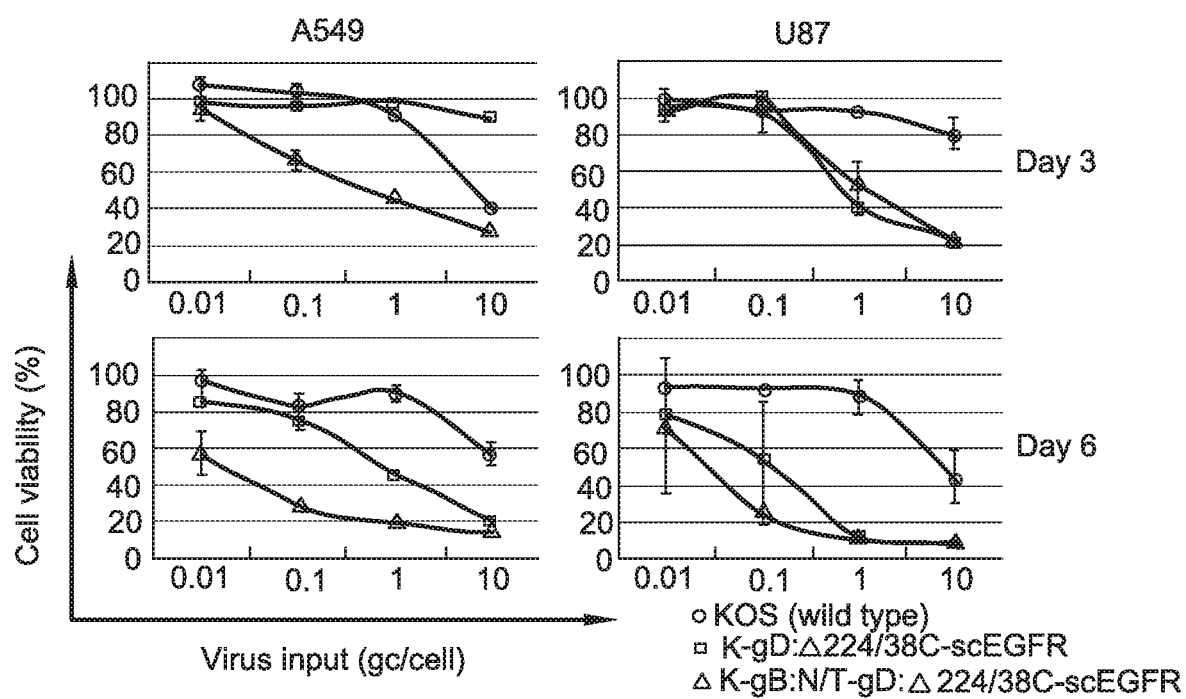

FIG. 7 depicts results of viability assays of cells infected with wild-type KOS, K-gD:Δ224/38C-scEGFR, or K-gB:N/T-gD:Δ224/38C-scEGFR. A549 or U87 cells were infected at 0.01-10 gc/cell for 3 or 6 days and cell viability relative to uninfected cells was determined by MTT assay. Data points are the means±SD of 6 replicates.

Figure 8A:
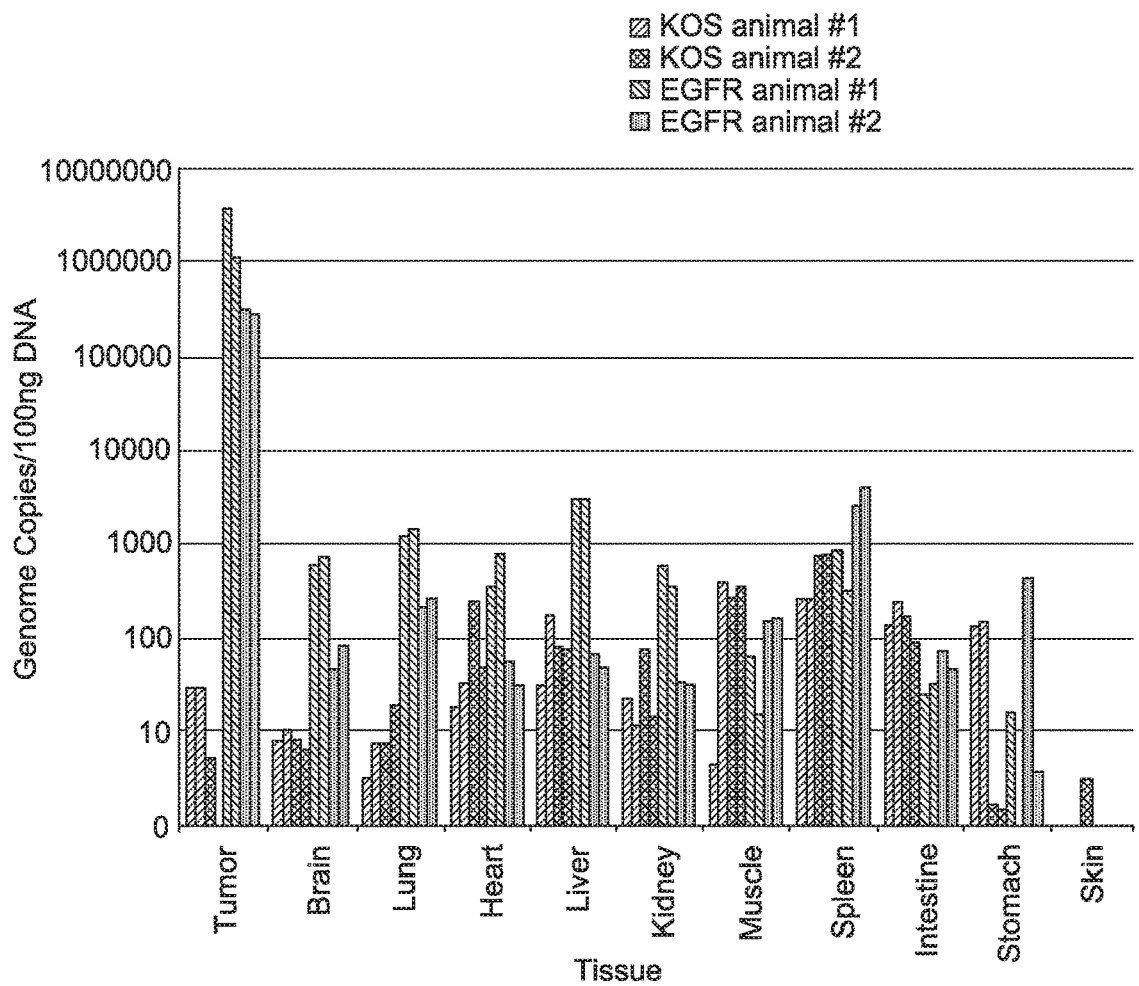

FIG. 8A depicts vector biodistribution results after in vivo administration of KOS or K-gB:NT-gD:A224/38C-scEGFR. U87 flank tumors in nude mice were allowed to grow to 700-1,000 mm3 in size, and 5×10$^8$ gc of KOS or K-gB:NT-gD:A224/38C-scEGFR were administered by tail-vein injection (n=2/virus). All animals were sacrificed 2 days later, and tumors and various organs were collected for DNA isolation and qPCR for the viral ICP47 gene. Virus load in the different tissues was calculated as gc/100 ng total DNA.

Figure 8B:
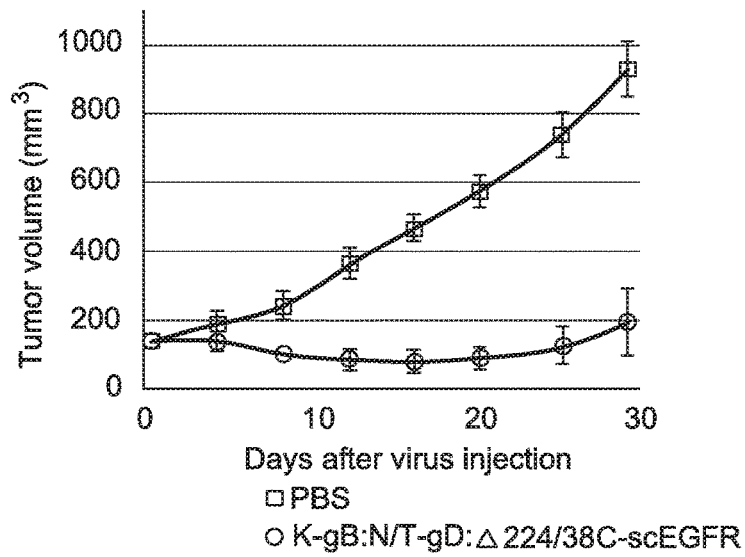

FIG. 8B depicts a plot of tumor size over time for U87 cells injected into the flanks of nude mice, with administration of K-gB:NT-gD:A224/38C-scEGFR or PBS as a negative control when tumor volumes reached 140 mm$^3$ (day 0). ANOVA analysis showed that the difference between the two groups was statistically significant (P<0.0001).

Figure 9:
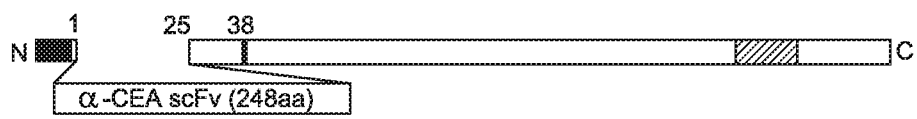

FIG. 9 provides a schematic representation of a gD mutant construct retargeted to CEA by an anti-CEA scFv insertion.

DETAILED DESCRIPTION OF THE INVENTION

The present invention relates to the surprising discovery that particular changes in HSV envelope proteins such as gH and gB can dramatically affect the kinetics of infection, such as efficiency of infection, rates of entry, and lateral spread of HSV among cells. In one embodiment, the invention provides an HSV vector comprising mutant gH glycoproteins, whereby said HSV vector exhibits lateral, i.e., "cell-to-cell" spread in cells lacking gD receptors.

The inventive vector can be an HSV-1 vector or an HSV-2 vector, but preferably is an HSV-1 vector. The vector can be derived from a wild-type HSV strain or from a laboratory strain (e.g., KOS) or mutant strain. In this context, the vector can be said to be "derived from" a strain by virtue of the mutagenesis of the vector being described with reference to the strain.

Typically, the mutant entry protein within the inventive HSV vector is a glycoprotein involved with viral entry, such as gB, gH, and the mutant HSV vector can comprise mutated versions of both. However, the mutant entry protein can be any protein effecting entry of the HSV vector into cells. In preferred embodiments, the mutant entry protein is other than gD, although the HSV vector can additionally comprise a mutant gD, such as containing a ligand or other desired mutation.

Preferred mutations of gB or gH glycoprotein for use in the inventive HSV vector occur at one or more of the following residues: gB:D285, gB:A549, gB:S668, gH:N753, and gH:A778. More preferably, the inventive HSV vector comprises mutations at both gB:D285 and gB:A549, at both gH:N753 and gH:A778, and/or at each of gB: S668, gH:N753, and gH:A778. More preferably, the HSV vector contains two or more of such mutations (e.g., 3 or more, 4 or more), and the inventive HSV vector can comprise mutations in all five of these residues. A preferred HSV vector has mutations at gB:285, gB; 549, gH:753, and gH:778.

The mutations are referred to herein relative to the codon (amino acid) numbering of the gD, gB, and gH genes of the HSV-1 strain KOS derivative K26GFP. The sequences for gB and gH of K26GFP differ from the sequences disclosed in GenBank #AF311740 (incorporated herein by reference) for gB and GenBank #X03896 (incorporated herein by reference) for gH as reflected in the following table:

TABLE 1

| | Amino acid position | AF311740 | K26GFP | Nucleotide position(s) | AF311740 | K26GFP |
|---|---|---|---|---|---|---|
| gB | 313 | T | S | 938-939 | ACG | AGC |
| | 315 | A | R | 943 | GCC | ACC |
| | 515 | H | T | 1,544 | CAC | CGC |
| | | X03896 | | | X03896 | |
| gH | 12 | I | L | 1,011 | ATT | CTT |
| | 110 | P | S | 1,305 | CCG | TCG |
| | 127 | T | I | 1,357 | ACC | ATC |
| | 138 | S | A | 1,389 | TCG | GCG |
| | 150 | A | T | 1,425 | GCC | ACC |
| | 532 | A | A | 2,573 | GCT | GCG |
| | 633 | R | R | 2,876 | CGT | CGC |

However, K26GFP may contain additional differences in the region of the gene corresponding to nucleotides 2,079-2,102 of GenBank X03896. Thus, it will be understood that the sequence of either KOS derivative K26GFP or GenBank Accession No. AF311740 can serve as a reference sequence for the gB mutations discussed herein. Also, the sequence of either KOS derivative K26GFP or GenBank Accession No. X03896 can serve as a reference sequence for the gH mutations discussed herein. However, the invention includes homologous mutations in gB and gH of any HSV strain.

Typically, the mutation of the entry protein for inclusion in the inventive HSV vector is a substitution mutation; however, the invention is not limited to substitution mutants. Especially preferred mutant gB or gH glycoproteins for use in the inventive HSV vector are selected from the group of substitution mutations consisting of gB:D285N, gB:A549T, gB:S668N, gH:N753K, gH:A778V. Preferably, the inventive HSV vector includes combinations of these substitutions (such as two or more of such substitutions (e.g., 3 or more, 4 or more, or all)), with the gB:D285N/gB:A549T double mutant, the gH:N753K/gH:A778V double mutant, and the gB: S668N/gH:N753K/gH:A778V triple mutant being preferred embodiments. gB:D285N/gB:A549T/gH:N753K/gH:A778V is the most preferred combination.

Efficiency of infection of a virus, such as an HSV vector of the present invention, reflects the number of viral particles required to infect a host cell, i.e., to produce a plaque. Efficiency of infection can be measured by any method deemed suitable by one of ordinary skill in the art, such as those described in the Examples provided herein. See also Uchida et al., *J. Virol.* 83: 2951-61 (2010). Efficiency of infection of an HSV vector of the present invention can be expressed as a ratio of plaques to total virus particles. In a preferred embodiment, the ratio is desirably as close to 1:1 (plaques to total virus particles) as possible, with infection efficiency optimized by maximizing the presence of active particles within a virus stock. For example, preferred vectors have a 1:100, 1:10, 1:5, or 1:3 infection rate. One of ordinary skill in the art will readily be able to consider the number or percentage of active particles as compared to total number of particles ("genome copy" or "gc" number). In other preferred embodiments, efficiency of infection of a retargeted HSV vector of the present invention is greater than that of a retargeted control HSV vector having a wild-type gB or gH protein. It will be understood that a sample of HSV vector used in testing efficiency of infection, whether a wild-type HSV or mutant HSV vectors of the present invention, desirably includes both active and inactive virus particles, and calculations of efficiency most appropriately are prepared based on numbers of active virus particles rather than on total (active and inactive) virus particles.

Certain HSV vectors in accordance with the present invention exhibit increased rate-of-entry relative to a control vector. Rate-of-entry reflects the amount of time at which the virus becomes resistant to inactivation by acidic wash of the cells, and can be measured by any method known to one of ordinary skill in the art, such as those described in the Examples provided herein. See also Uchida et al., *J. Virol.* 83: 2951-61 (2010). Another method for determining rate of entry is measurement of ICP4 expression at 6-8 hours post-infection. In particular, rate-of-entry assays of the present HSV vectors are typically carried out by incubating Vero cells with HSV vectors at 4° C. for 30 minutes, and then shifted to 30 or 37° C. for various intervals, such as 2, 3, 5, 10, 15, 20, 30, 40, 45, 50, 60, 120, or 180 minutes, followed by acidic wash. One of ordinary skill in the art will understand that rate-of-entry assays for other vectors will necessarily be conducted in suitable cells having appropriate receptors. An appropriate control vector is a retargeted HSV vector that has a wild-type gB or gH protein. The resulting cultures are overlaid with methylcellulose-containing media and incubated for an interval such as 48 hours before counting plaques. In other preferred embodiments, rate of entry of a retargeted HSV vector of the present invention is greater than that of a retargeted control HSV vector having a wild-type gB or gH protein. For example, the rate of entry can be increased by 10%, 15%, 20%, 25%, 30%, 35%, 40%, 45%, 50% or more than 50% as compared with wild-type HSV. Exemplary vectors in accordance with the present invention, thus, exhibit at least 25% increased rate-of-entry after 20 minutes when assayed at either 30° C. or 37° C. in Vero cells after first incubating at 4° C. relative to a wild-type HSV.

HSV vectors of the present invention can enter cells either by direct infection or by lateral spread and, in some embodiments, the inventive HSV can infect and/or spread to cells normally resistant to HSV infection. In preferred embodiments, HSV vectors of the present invention are capable of both direct entry and lateral spread, although in some embodiments, the vectors may have similar capacity or increased capability for one type of entry (i.e., direct vs. lateral) as compared to a wild type HSV, with similar or decreased capability for the other type of entry.

The inventive HSV vector desirably is able to enter a cell, whether by lateral spread or otherwise, normally resistant to HSV entry. In certain embodiments, the inventive HSV vector can directly infect a cell via interaction with nectin-2, nectin-3, nectin-4 or one or more other non-HSV receptors. For example, an HSV vector can infect a cell via interaction of gD, and preferably via interaction of gD and gC with a cell surface protein other than or in addition to nectin-1, HVEM, and heparin sulfate/chondroitin sulfate proteoglycans. In such HSV vectors, the inventive HSV vectors can comprise a viral envelope having one or more mutant envelope proteins other than gD or gC. In other embodiments, the inventive HSV vector exhibits lateral spread in cells lacking gD receptors. Mutant forms of gH, for example as described herein, can be incorporated into such HSV to effect such enhanced lateral spread ability.

In addition to having the mutant entry protein or proteins, the inventive HSV also can include a non-native ligand specific for a protein or other suitable binding site present at the surface of a predetermined cell type. To contact the cell, the ligand preferably is attached to the surface of the HSV virion, such as by incorporation into a viral envelope protein or glycoprotein (such as gC, gD, and the like). This can be achieved by expression as a recombinant fusion protein, for example a fusion with a HSV surface protein or glycoprotein containing the ligand, or by chemical crosslinking of the ligand to the virion or by the establishment of high-affinity biochemical interaction of the virus envelope with the ligand, for example mediated through biotin-avidin binding.

The ligand can be any suitable agent that binds the surface of the predetermined cell. The ligand typically is proteinaceous and can constitute a natural binding partner for a cell surface protein (e.g., EGF), a portion of an antibody (e.g., a single chain antibody (scFv), a single domain antibody (VHH), or other ligand), or other binding agent. Where the predetermined cell is a cancer cell, a ligand can target a protein present on the cancer cell. For example, the cancer cell can display a receptor such as EGFR, EGFRvIII, CEA, and ClC-3/annexin-2/MMP-2, and the ligand can target such a receptor, i.e., the ligand can be capable of specifically binding such protein. The cell can be any contemplated cancer cell, although in preferred embodiments, the cancer cell is a lung epithelial carcinoma cell, a colon adenocarcinoma cell, a pancreatic adenocarcinoma cell, a glioblastoma cell, an astroglioma cell, a vulvar epithelial carcinoma cell, or a breast carcinoma cell. Preferably, the cancer cell is in a mammal, such as a human.

Replacement of a portion of gD (such as of residues 61-218) with a scFv targeting a receptor such as HER-2 (also referred to as neu or erbB-2) can serve as a ligand for targeting certain cancer cells (those overexpressing HER-2). Similarly, a scFv or other ligand, binding to the tumor-specific marker carcino-embryonic antigen (CEA) or the tumor-associated EGFR can be employed and insertion sites in gD can be between residues 1 and 25 or between residues 24 and 25. Further information concerning the ligand, as well as engineering HSV vectors containing ligands, is discussed in international patent publication WO 1999/006583, the disclosure of which is incorporated herein by reference. When expressed as a fusion with an envelope protein, scFvs or VHHs are generally preferred over other types of ligands. scFvs and VHHS that exclusively recognize mutant versions of the EGFR, such as an internally deleted version called EGFRvIII, are preferred targeting ligands. EGFRvIII and other mutant EGFR versions are specifically expressed on cancer cells and not on normal cells. EGFRvIII-specific antibodies, scFvs and VHHs have been described in the literature (Kuan et al, *Int. J. Cancer*, 88, 962-69 (2000); Wickstrand et al., *Cancer Res.*, 55(14): 3140-8 (1995); Omidfar et al., *Tumor Biology*, 25:296-305 (2004)).

In addition to having the mutant entry protein and the ligand, the inventive HSV vector can be further modified from a wild-type HSV. For example, in some embodiments, the inventive HSV vector can be used as an oncolytic virus. For such application, the HSV vector genome can be modified similarly as HSV vectors currently under investigation as oncolytic vectors. Also, the genome of the inventive vector can be engineered to contain microRNA target sequences, such as miR21, miR124, and/or miR128, which can be employed to achieve preferential HSV replication in tumor cells (see Lee et al., *Clin. Cancer Res.*, 15(16), 5126-35 (2009); Edge et al., *Mol. Ther.*, 16(8), 1437-43 (2008); Caewood et al., *Plos Pathogens*, 5(5), e1000440 (2009)). In this respect, control of virus replication by cellular microRNAs can be achieved by insertion of microRNA target sequences into untranslated regions of essential viral genes. MicroRNA recognition of the targeted viral mRNA causes degradation of that viral mRNA (or blocks its translation). Thus the virus will not be produced in normal cells that contain the regulatory microRNA, but will be produced in (e.g.) tumor cells that do not contain the microRNA. Alternatively, the genome can be rendered replication incompetent and engineered to express one or more transgenes (see, e.g., U.S. Pat. Nos. 5,804,413 and 7,531, 167, which are incorporated herein by reference), which can encode proteins or polypeptides or biologically-active RNAs (such as microRNA, interfering RNA, etc.). Accordingly, genome of the inventive HSV vector, whether replication-competent (oncolytic) or replication-defective, can comprise one or more exogenous expression cassettes (i.e., containing encoding-sequences in operable linkage with promoters, enhancers, and other suitable regulatory elements), such as encoding a transgene expressing marker (such as green fluorescent protein), an agent that enhances tumor killing activity (such as TRAIL or TNF), or other therapeutically-important gene product.

Further, the inventive HSV vector can have one or more viral envelope glycoproteins impaired for binding to its natural receptor. In some embodiments, one or more viral envelope glycoproteins can be deleted altogether. In preferred embodiments, the viral envelope glycoprotein that is impaired or deleted is gC or gD.

The inventive HSV vector can be made by any suitable method, which are known to those of ordinary skill in the art. Typically, the inventive HSV vector will be constructed using recombinant DNA technology, whereby a gene encoding the mutant entry protein replaces the corresponding wild-type (or source) copy of the entry protein gene. Accordingly, HSV vectors according to the invention having a mutant gB and/or gH protein have a gene encoding the mutant gB and/or gH protein, respectively, and lack a gene encoding wild-type gB and/or gH, respectively.

To facilitate the manufacture of the inventive HSV vector, the invention provides a DNA molecule comprising a sequence of nucleic acids encoding a mutant entry protein suitable for inclusion into the inventive HSV vector. For example, the DNA molecule can encode any mutant gB glycoprotein described herein, such as having a mutation at one or more of the following residues: gB:D285, gB:A549, and/or gB:S668 (such as gB:D285N, gB:A549T, and/or gB:S668N). Similarly, the DNA molecule can encode a mutant gH glycoprotein as described herein, such as having a sequence of nucleic acids encoding a mutant gH glycoprotein having a mutation at one or more of the following residues: gH:N753 and/or gH:A778 (such as gH:N753K and/or gH:A778V).

The DNA molecule can be in any suitable form, such as a plasmid, cosmid, or other construct. The DNA molecule can also include other sequences suitable for propagation (ori sites), expression (e.g., promoters, enhancers, IRES sites and other regulatory sequences) or engineering (e.g., cassettes encoding toxins, markers or tags, restriction enzyme recognition sites, etc.).

The genetic constructs, and the HSV vectors, of the present invention can be constructed using standard techniques. For example, a relatively new technique is manipulation of the HSV genome in bacteria as bacterial artificial chromosomes (BACs) (see, e.g., Gierash et al., *J. Virol. Meth.*, 135, 197-206 (2006)). That the entire HSV genome is published (see, e.g., GenBank #X14112 (strain 17), and portions from other strains are similarly published (e.g., GenBank #AF311740 for gB and #X03896 for gH), further facilitates the construction of the inventive HSV vectors and genetic constructs.

Generally, the inventive HSV vector is most useful when enough of the virus can be delivered to a cell population to ensure that the cells are confronted with a suitable number of viruses. Thus, the present invention provides a stock, preferably a homogeneous stock, comprising the inventive HSV vector. The preparation and analysis of HSV stocks is well known in the art. For example, a viral stock can be manufactured in roller bottles containing cells transduced with the HSV vector. The viral stock can then be purified on a continuous nycodenze gradient, and aliquotted and stored until needed. Viral stocks vary considerably in titer, depending largely on viral genotype and the protocol and cell lines used to prepare them. Preferably, such a stock has a viral titer of at least about $10^5$ plaque-forming units (pfu), such as at least about $10^6$ pfu or even more preferably at least about $10^7$ pfu. In still more preferred embodiments, the titer can be at least about $10^8$ pfu, or at least about $10^9$ pfu, and high titer stocks of at least about $10^{10}$ pfu or at least about $10^{11}$ pfu are most preferred. Such titers are established using cells that express the targeted receptor.

The invention additionally provides a composition comprising the HSV vector and a carrier, preferably a physiologically-acceptable carrier. The carrier of the composition can be any suitable carrier for the vector. The carrier typically will be liquid, but also can be solid, or a combination of liquid and solid components. The carrier desirably is a pharmaceutically acceptable (e.g., a physiologically or pharmacologically acceptable) carrier (e.g., excipient or diluent). Pharmaceutically acceptable carriers are well known and are readily available. The choice of carrier will be determined, at least in part, by the particular vector and the particular method used to administer the composition. The composition can further comprise any other suitable components, especially for enhancing the stability of the composition and/or its end-use. Accordingly, there is a wide variety of suitable formulations of the composition of the invention. The following formulations and methods are merely exemplary and are in no way limiting.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described.

In addition, the composition can comprise additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the vector and physiological distress. Immune system suppressors can be administered with the composition method to reduce any immune response to the vector itself or associated with a disorder. Alternatively, immune enhancers can be included in the composition to upregulate the body's natural defenses against disease. Antibiotics, i.e., microbicides and fungicides, can be present to reduce the risk of infection associated with gene transfer procedures and other disorders.

HSV vectors and compositions as described herein can be used in methods of killing a cancer cell. In such methods, an HSV vector or composition as described herein is applied to a cancer cell that has been removed from or is present in an organism, such as a mouse, rat, rabbit, cat, dog, pig, cow, chicken, monkey, or human, using methods known to one of ordinary skill in the art. In some exemplary embodiments, the cancer cell is a lung epithelial carcinoma cell, a colon adenocarcinoma cell, a pancreatic adenocarcinoma cell, a glioblastoma cell, an astroglioma cell, a vulvar epithelial carcinoma cell, or a breast carcinoma cell.

For treating cancer cells in vivo, a preferred embodiment of the inventive HSV comprises mutations in gB and/or gH as described herein, whereby efficient entry of the vector into tumor cells is achieved. Furthermore, such vectors additionally desirably comprises a targeting ligand as described to alter the HSV tropism to target cancer cells preferentially. The use of a cancer-specific ligand can facilitate treatment of disseminated cancer and systemic delivery of the HSV, although for treating solid tumors, intratumoral delivery, such as stereotactic injection, can be employed. For example, Examples 13 and 14 reveal preferential tumor targeting using EGFR- and CEA-specific ligands, but other tumor antigens can be similarly employed. Such an HSV further can comprise microRNA target sequences to facilitate preferential replication in cancer/tumor cells. The HSV thus can home to tumor/cancer cells preferentially, minimizing infection of non-targeted cells, enter the tumor/cancer cells efficiently, and preferentially replicate in tumor/cancer cells as opposed to healthy cells. Furthermore, such an HSV can be engineered to express an anti-cancer/tumor factor in tumors to further effect killing of the cancerous/tumor cells in vivo. Additionally, a replication-defective HSV can be engineered to target other types of cells to efficiently and cell-specifically deliver therapeutic genes for other diseases.

The following examples further illustrate the invention but, of course, should not be construed as in any way limiting its scope.

Example 1

This example describes the identification of a hyperactive gB-mutant, gB:D285N/A549T ("gB:N/T") through use of various cell lines modified for receptivity to HSV infection.

Baby hamster kidney J1.1-2 and murine melanoma B78H1 cells (as described in *J Virol* 83, 2951-2961) have been shown to be resistant to HSV infection due to the absence of gD receptors (*J Virol* 72, 9992-10002; *J Virol* 76, 2424-2433; *Mol Ther* 3, 160-168). A mutant version of nectin-1, QN76-77AA/M85F, that is severely impaired for binding to gD and thus fails to support HSV entry, was previously described by Struyf et al. (*J Virol* 76, 12940-12950) and is referred to here as TMC (Triply Mutated HveC). Clonal TMC-expressing J and B78 cell lines were created by stable transfection and designated J/TMC and B78/TMC. J/TMC and B78/TMC cells were established by transfection of J1.1-2 or B78H1 cells with plasmid pcDNA3TMC and selection for resistance to 0.4 mg/ml or 0.8 mg/ml G418, respectively. The TMC expression plasmid pcDNA3TMC was created by replacement of a V-domain-encoding fragment of pBG38 (*Science* 280, 1618-1620) with the corresponding fragment of pTMC153-his (*J Virol* 80, 138-148). Clonal lines obtained by limiting dilution or cylinder cloning methods were confirmed for expression of the introduced receptor cDNAs in >95% of the cells by indirect immunofluorescence.

J/TMCΔC cells were established by transfection of J1.1-2 cells with plasmid pcDNA3TMCΔC and selection with 0.4 mg/ml G418. Plasmid pcDNA3TMCΔC, encoding TMC deleted for both C-domains, was created by deleting the coding sequences for nectin-1 codons 148 to 336 from pcDNA3TMC.

The virus mutant K26-gD:R222N/F223I (*J Virol* 83, 2951-2961; *Virology* 360, 477-491), abbreviated here as K26-gD:2/3NI, is a mutant of K26GFP (*J Virol* 72, 7563-7568) and has a highly diminished ability to use nectin-1 for infection due to a pair of mutations in gD, but is largely unimpaired for infection through HVEM; it expresses a VP26-GFP fusion protein (*J Virol* 72, 7563-7568) facilitating the detection of virus infection and growth. K26-gD:2/3NI was challenged for growth on J/TMC or B78/TMC cells by reiterative high-MOI infection and progeny amplification on HVEM-expressing J (J/A) cells.

Two separate selections were carried out. In the first, J/TMC cells were inoculated with K26-gD:2/3NI at 1,000 pfu/cell and rinsed after 8 h with acidic buffer (Table 1, Exp 1). Progeny virus harvested 2 d later from the cells and medium was expanded on J/A cells for infection of J/TMC cells at 100 pfu/cell, followed by acid treatment at 8 h. Progeny virus was harvested as before and used for plaque purification by limiting dilution on J/TMC cells. The second selection (Table 2, Exp 2) was performed in a similar manner with the following modifications. B78/TMC cells were inoculated with the same initial virus at 100 pfu/cell followed by expansion on J/A cells, progeny virus was passaged twice more on B78/TMC cells and once on J/TMCΔC cells. Plaque purifications were performed on B78/TMC cells.

Following the above selections, virus was isolated from a number of individual J/TMC and B78/TMC plaques, purified, and characterized. Direct sequencing was used to identify mutations in the gD gene of seven isolates derived from the first experiment and eight from the second. As shown in Table 1, 10 of the 15 isolates had one or two new missense mutations in the gD ORF in addition to the parental 2/3NI mutations. Distinct amino acid substitutions were found in isolates from the first (A185T) and second selection (Q178H), and one isolate contained both substitutions. However, five of the seven isolates from the first experiment harbored no new gD mutations, suggesting that these viruses had undergone alterations outside the gD gene.

TABLE 1 gD mutations in selected virus isolates[a].

| Group | Substitution (parental + new)[b] | New base change[b] | Frequency[c] | Isolate #[d] |
|---|---|---|---|---|
| | | Exp 1 (2 passages) | | |
| 1 | R222N/F223I | — | 5/7 | A |
| 2 | R222N/F223I + A185T | GCC→ACC | 2/7 | B |
| | | Exp 2 (4 passages) | | |
| 3 | R222N/F223I + Q178H | CAG→CAT | 7/8 | C |
| 4 | R222N/F223I + Q178H/A185T | CAG/GCC→CAT/ACC | 1/8 | D |

[a]K26-gD:2/3NI was passaged twice or four times through TMC-expressing cells and progeny viruses were cloned by limiting dilution on J/A cells.
[b]Amino acid or nucleotide changes in individual isolates.
[c]Number of isolates with the indicated mutation/total number of analyzed isolates in each experiment.
[d]Designation of representative isolate from each of the groups.

One representative isolate from each of the four gD-mutant groups (Table 1) was purified by repeated limiting dilution on J/A cells. The isolates were amplified on J/A cells and their infection profiles established on B78 cells expressing HVEM (B78/A), nectin-1 (B78/C), TMC, or no gD receptor. Infections were performed with equal numbers of viral genome copies (gc) determined by real-time quantitative PCR (*J Virol* 76, 12940-12950). Control infections included K26-gD:2/3NI and its wild-type gD parent, K26GFP (*J Virol* 72, 7563-7568). Cells were infected for 8 h and expression of the tegument protein VP16 was visualized by indirect immunofluorescence rather than GFP fluorescence in these assays because the intensity of the GFP signal varied among the isolates and the parental viruses.

Neither K26GFP nor the restricted K26-gD:2/3NI virus showed infection of B78H1 cells even at 1,000 gc/cell, consistent with the absence of gD receptors on these cells. In agreement with previous findings (*J Virol* 83, 2951-2961), K26-gD:2/3NI showed substantially reduced infection of B78/C, but not B78/A cells compared to K26GFP. Infection of B78/TMC cells by K26GFP was observed only at the highest gc input, while infection by K26-gD:2/3NI was undetectable, thus validating the use of this virus-receptor combination for the selection of gain-of-function mutants. Isolate A showed a similar level of infection on B78/A cells as K26GFP and K26-gD:2/3NI. However, although this isolate had the same gD ORF as K26-gD:2/3NI, it infected B78/C cells with an efficiency similar to that of wild-type gD virus rather than at the much lower level observed with K26-gD:2/3NI. This unanticipated result indicated that other virus glycoproteins involved in the entry process had been altered. On B78/TMC cells, isolate A showed a dramatic increase in infectious activity over its parent, as expected, but also greater activity than K26GFP. Surprisingly, unlike K26GFP and K26-gD:2/3NI, isolate A was capable of infecting unmodified B78H1 cells, suggesting the acquisition of mutations that render infection independent of known gD receptors. ICP4 staining at 6 h post-infection (hpi) showed essentially the same trend, indicating that the changes in isolate A principally facilitated virus entry rather than replication.

To quantify these results and identify potential differences between isolate A and the gD-altered isolates B-D, the plaque-forming activities of the four isolates and the two control viruses on the panel of B78 cell lines were compared. The results of triplicate titrations of each virus on each cell line, expressed as plaque-forming units per genome copy (pfu/gc) (FIG. 1), mirrored those of the single-round infection assays for isolate A. Thus, all four isolates showed increased plaque formation on B78/C cells compared to their K26-gD:2/3NI parent virus. Unlike the parent virus, all four formed plaques on B78/TMC and B78H1 cells. In addition, the shared A185T substitution in gD of isolates B and D appeared to have a general enhancing effect on plaque formation, consistent with a previous report that A185T increases the efficiency of viral cell-to-cell spread in a gD receptor-independent manner (*J Virol* 74, 11437-11446).

Together, these results indicated that the four isolates had similar mutations outside the gD gene and that the identified mutations in gD were not the primary cause of the acquired ability of these viruses to grow on B78/TMC and B78H1 cells. Furthermore, it is noteworthy that the specific infectious activities (pfu/gc) of the four isolates were very similar on B78/TMC and B78H1 cells, indicating that the impaired gD receptor TMC did not play a key role in the original selection of these isolates.

Direct sequencing revealed that each of the four isolates harbored the same two missense mutations in the gB ORF: D285N and A549T. The gH and gL ORFs of isolate A, were also sequenced, with the exception of an extremely GC-rich 20-nucleotide portion of gH (positions 1983-2102 in GenBank accession number X03896). No changes were found in either gene.

These results show that the double missense mutation in gB, referred to hereafter as N/T, was most likely responsible for the acquired phenotypes of the selected isolates.

Example 2

This example characterizes functional changes caused by the N/T mutation as they relate to the infectious properties of the virus, particularly viral entry via proteins other than nectin-1.

To confirm that new gD mutations in isolates B-D were not responsible for the extended tropism of these viruses, the cloned gD gene of each isolate was expressed and evaluated to determine whether incorporation of its product into a gD-null virus would mimic the changes in host-cell range observed with the complete isolate. The results of these transient complementation assays, conducted as described in *J Virol* 74, 2481-2487, showed that none of the newly acquired mutations in the gD genes of isolates B-D substantially altered virus infection of any of the four cell lines. Notably, the mutant gD alleles yielded no detectable infection of B78/TMC cells although two of them were isolated following selection on these cells. Furthermore, the acquired mutations showed minimal suppression on B78/C cells of the nectin-1-specific defect caused by the parental 2/3NI mutations. These results supported the suggestion that the gain-of-function phenotypes of the different isolates were principally the result of changes outside the gD ORF.

Next, to evaluate the effects of the N/T mutations, a gB-null virus, KΔT (*J Virol* 61, 714-721), was rescued by homologous recombination with wild-type and N/T-mutant gB plasmids and plaque purification on non-complementing Vero cells (African green monkey kidney cells). Vero cells were co-transfected with KΔT (*J Virol* 61, 714-721) viral DNA and plasmids pgB1:wt or pgB1:D285N/A549T, followed by plaque purification through three rounds of limiting dilution on Vero cells. Isolates designated K-gB:wt and K-gB:N/T (K-gB:N/T), respectively, were confirmed by DNA sequencing through the entire gB and gD ORFs. Plasmid pgB1:wt contains the gB ORF and flanking regulatory sequences from K26GFP (*J Virol* 72, 7563-7568); mutant counterparts, including pgB1:D285N/A549T, were created by replacement of appropriate fragments of pgB1:wt with the corresponding fragments of PCR products generated on DNA from selected virus isolates.

Because gB contributes to virus attachment to cells by binding to glycosaminoglycans ("GAGs") on the cell surface, gD receptor-deficient CHO-K1 cells and their GAG-deficient derivative pgsA-745 cells (*Prot Natl Acad Sci USA* 82, 3197-3201) were used to determine whether enhanced infection by gB:N/T was dependent on GAG binding. At 8 hpi, K-gB:N/T produced readily detectable infection of CHO-K1 cells at a virus input of 100 or more gc/cell, whereas no infection by K-gB:wt was seen at a 10-fold higher dose and limited infection at a 100-fold higher dose. At 24 hpi, K-gB:N/T produced foci of infected CHO-K1 cells, indicative of direct cell-to-cell spread, while a 100-fold higher dose of K-gB:wt yielded only individual infected cells and very small foci. On GAG-deficient pgsA-745 cells, infection by K-gB:wt was barely detectable even at 24 hpi at the highest virus input. In contrast, infected cells were distinguishable at a 100-fold lower dose of K-gB:N/T at both 8 and 24 hpi. Together, these results demonstrated that gB:N/T enables infection of gD receptor-negative cells and indicated that this effect was not due to increased binding of gB to GAGs. Using a direct assay for virion attachment, gB:N/T mutations did not enhance GAG-dependent or GAG-independent virus adsorption to cells.

Given the absence of known gD receptors on CHO-K1 cells (*Cell* 87, 427-436), K-gB:N/T was analyzed to determine whether gD is required for the enhanced infection of these cells. A gD-null virus was derived from K-gB:N/T, designated K-gB:N/TΔgD, by replacement of the complete gD ORF with that of EGFP. CHO-K1 cells were infected with 1,000 gc/cell of K-gB:N/T or K-gB:N/TΔgD and stained for VP16 at 16 hpi. The results showed that gD is indispensable for infection of CHO-K1 cells by K-gB:N/T. The requirement for gD in K-gB:N/T infection of CHO-K1 cells raised the possibility that these cells express minor or cryptic gD receptors on their surface that can serve as HSV-1 entry receptors conditional to the presence of the gB:N/T double mutation. Nectin-3 was considered as a candidate based on a previous report by Cocchi et al. that nectin-3 can mediate entry of HSV harboring a particular combination of gD mutations (*J Virol* 78, 4720-4729). To perform an infection blocking assay, CHO-K1 cells were incubated with rat anti-mouse nectin-3 (Cell Sciences) or rat anti-mouse nectin-4 (R&D Systems) mAbs (both IgG2a) or PBS for 1 h at RT, and then infected with K-gB:N/T at 3,000 gc/cell for 2 h at 37° C. followed by acid treatment. Infections were assessed at 16 hpi as described above. The results showed that anti-nectin-3, but not isotype-matched anti-nectin-4, reduced infection by K-gB:N/T in a dose-dependent manner; phase-contrast images indicated that this was not due to anti-nectin-3-mediated cell detachment. These observations suggested that nectin-3 plays an essential role in gB:N/T mutant virus infection of CHO-K1 cells, most likely by functioning as a receptor for gD.

Indirect immunofluorescence was performed as described previously (*J Virol* 83, 2951-2961), using goat anti-mouse nectin-3 or nectin-4 polyclonal antibodies (R&D Systems) (1 μg/ml) as primary antibodies and Cy3-conjugated rabbit anti-goat IgG (Sigma) (1:400) as secondary antibody. Immunofluorescence analysis demonstrated the presence of nectin-3 on the surface of CHO-K1 cells.

Since nectin-3 appeared to enable K-gB:N/T infection of CHO-K1 cells, other nectin-family members were evaluated for this function. Increased infection by both K-gB:wt and K-gB:N/T was seen on CHO-K1 cells that overexpress human nectin-2 (CHO/Nec2) (*Virology* 246, 179-189) or nectin-4 (CHO/Nec4) compared to unmodified CHO-K1 cells, indicating that these nectins can act as HSV entry receptors, but infection was approximately 100-fold higher in each case for K-gB:N/T than for K-gB:wt; neither virus infected any of these cell lines as efficiently as they infected CHO-K1 cells expressing human nectin-1 (CHO/C (*Science* 280, 1618-1620)). These data indicated that gB:N/T facilitates the use of multiple members of the nectin family for viral entry, suggesting that the gB mutations act in a general manner to enhance virus infection through weak gD-receptor interactions. A similar effect was seen in a comparison of K-gB:wt and K-gB:N/T infection of B78/TMC cells where the gD binding-impaired TMC mutant of nectin-1 represented the weak receptor.

Example 3

This example demonstrates accelerated viral rate of entry by the gB:N/T mutant allele.

Since mutations in gB have previously been shown to alter the kinetics of viral entry (*J Virol* 63, 730-738; *Virology* 122, 411-423; *Virology* 137, 185-190), rate-of-entry assays were performed to determine whether the gB:N/T mutations might act in this manner. Nectin-1-expressing cells (B78/C) were used for these experiments because these cells are susceptible to both the wild-type and the mutant virus after 24 h of virus/cell co-incubation However, under those conditions these cells showed no clear difference in infection efficiencies between K-gB:wt and K-gB:N/T. B78/C cells were incubated with K-gB:wt or K-gB:N/T at 200 pfu per well at 4° C., washed thoroughly, incubated at 37° C. or 30° C. for 0-60 min, and extracellular virus was inactivated by low-pH treatment. The cells were then overlain with methylcellulose-containing media and incubated at 37° C. for 3 days to allow plaque formation. At 37° C., entry of gB:wt virus progressed steadily over time whereas entry of the mutant virus in the first 3 min exceeded that of the wild-type virus in 60 min (FIG. 2A). However, following this initial phase of rapid entry by the mutant virus, additional entry was limited such that at 60 min nearly equal numbers of the two viruses had entered the cells. This observation indicated that the dramatic differences at the early time points reflected a difference in virus entry kinetics rather than in virus input. At 30° C., entry also proceeded more rapidly for K-gB:NIT than for K-gB:wt although the extent of entry was lower overall than at 37° C. These results demonstrated that the gB:N/T mutations accelerate virus entry via the natural gD receptor nectin-1.

HSV-1 entry into gD receptor-transduced B78 cells reportedly takes place by a low-pH-independent endocytic pathway (*J Virol* 79, 6655-6663), whereas entry into Vero cells occurs by membrane fusion at the cell surface (*Proc Nat'l Acad Sci USA* 84, 5454-5458; *J Virol* 63, 3435-3443); entry into receptor-transduced CHO-K1 cells is mediated by a low-pH-dependent endocytic pathway (*J Virol* 77, 5324-5332; *J Virol* 78, 7508-7517). To determine whether the gB:N/T mutations accelerate entry through each of these different pathways, the rate-of-entry assays were repeated on Vero and CHO/C cells. As shown in FIG. 2B, the results on Vero cells at 37° C. were similar to those on B78/C cells although both viruses showed a delay in early kinetics compared to B78/C cells. As on B78/C cells, the entry kinetics were slower at 30° C., but the 60 min entry level of K-gB:N/T was as high as the maximum reached at 37° C. Since CHO/C cells do not form well-defined plaques, the rates of entry on these cells were assessed by anti-VP16 staining at 8 h post acidic wash to visualize infected cells. B78/C cells were included for comparison. The entry kinetics of both viruses were similar on the two cell lines and consistent for B78/C cells with the results of FIG. 2A. K-gB:wt showed a gradual increase in infection, reaching a maximum at 30-60 min, while as little as 3 min sufficed for near-maximum infection by K-gB:N/T. These results demonstrated that the gB:N/T mutations accelerate virus entry into receptor-bearing cells regardless of the pathway used by wild-type virus.

Transiently complemented gB-null virus was used to determine whether the individual mutations of gB:N/T affected the rate of virus entry. Vero cells were transfected with expression plasmids for gB:N/T, gB:D285N, and gB:A549T, the cells were infected the next day with KΔT, and supernatants harvested the following day were used for rate-of-entry assays on B78/C and Vero cells.

Rate-of-entry assays were performed as described previously (*J Virol* 63, 730-738) with modifications. Cells were incubated with viruses at 4° C. for 30 or 60 min and washed three times with cold PBS. The cells were then shifted to 37 or 30° C. for various intervals followed by acid treatment. The cultures were incubated at 37° C. and stained for VP16 expression at 8 h (primary infection) or 48-72 h (plaque formation).

The results of this assay showed that entry was accelerated on both cell lines by either of the single mutant gBs compared to wild-type gB. The A549T version of gB displayed a somewhat greater effect than the D285N version, and the double mutant gB mediated slightly more entry in 10 min than either of the single mutants; these differences were clearer on Vero cells than on B78/C cells which was not surprising given the observation that the majority of K-gB:N/T virus entry into B78/C cells occurred in the first few minutes (FIG. 2A) while entry into Vero cells took place at a slower pace (FIG. 2B). These results indicated that each of the gB:N/T mutations contributed, albeit unequally, to the phenotype of the double mutant protein.

Example 4

This example demonstrates enhancement of retargeted HSV infection by the gB:N/T mutant allele.

HSV infection has been retargeted by ablation of the native receptor-recognition functions of gD and insertion of recognition elements for novel receptors (*Proc Natl Acad Sci USA* 103, 5508-5513; *J Virol* 82, 10153-10161; *Proc Natl Acad Sci USA* 106, 9039-9044). However, the efficiency of these retargeted infections has been reported to be lower than that of natural infection through authentic receptors. To determine whether efficiency was improved over retargeted HSVs containing gB:wt, gB:N/T was analyzed for its effect on targeted receptor-dependent and -independent ("off-target") infection. A gD-null derivative of K-gB:wt, designated K-gB:wtΔgD, was generated by replacement of the gD ORF with that of EGFP as done earlier to produce K-gB:N/TΔgD. Thus, K-gB:wtΔgD and K-gB:N/TΔgD were produced by co-transfection of VD60 cells with plasmid pΔgD-EGFP and viral DNAs of K-gB:wt or K-gB:N/T, respectively, with subsequent purification of green-fluorescent plaques on VD60 cells.

Using equal amounts of these two gD-null viruses (pfu determined on gD-complementing VD60 cells as described in *J Virol* 62, 1486-1494), transient complementation assays were performed with a retargeted gD construct, pgD:3C/Δ711/38C-scEGFR, containing mutations that severely impair virus infection through nectin-1 (A3C/Y38C) (*J Virol* 79, 1282-1295, 2005; *J Virol* 83, 2951-2961, 2009) and HVEM (deletion of residues 7-11), and an insertion specifying a single-chain antibody (scFv) directed against the epidermal growth factor receptor (EGFR) between residues 24 and 25. The retargeting plasmid pgD:3C/Δ711/38C-scEGFR was generated by insertion of the 528 scFv sequence (*Clin Cancer Res* 12, 4036-4042) into plasmid pgD:3C/Δ711/38C-NE (0.1 Virol 79, 1282-1295).

The retargeted gD construct enabled infection exclusively of EGFR-transduced CHO-K1 cells (CHO/EGFR) by K-gB:N/TΔgD but not K-gB:wtΔgD, while the parental wild-type gD construct complemented both viruses for infection of CHO-K1 cells expressing the natural HSV receptors HVEM (CHO/A cells) or nectin-1 (CHO/C), but not for infection of CHO/EGFR cells.

As described earlier, entry of the gB:N/T virus into nectin-1-bearing cells was markedly accelerated compared to wild-type virus (K-gB:wt), suggesting that the gB:N/T double mutation affects a rate-limiting step in entry. The gB:N/T double mutation was combined with an EGFR-retargeted gD allele, gD:Δ224/38C-scEGFR, in a wild-type virus background. The resulting virus entered EGFR-transduced J1.1-2 cells (J/EGFR) that lack authentic HSV receptors approximately 100-fold more efficiently than the same virus lacking the gB double mutation. Furthermore, the double recombinant virus entered EGFR-transduced J1.1-2 cells at least 10,000-fold more efficiently than J1.1-2 cells transduced with the natural entry receptors, HVEM or nectin-1. Thus the gB double mutation increased the efficiency of retargeted infection without yielding significant "off-target" infection through the natural HSV entry receptors. In addition, the double recombinant virus entered a number of tumor cell lines expressing EGFR with similar efficiencies as wild-type virus entering these lines via the natural receptors. On most of these cell lines as well, the retargeted virus lacking the gB double mutation showed approximately 100-fold less entry.

These results strongly suggested that gB:N/T can augment targeted receptor-dependent HSV infection without detectably increasing off-target infection and hence, that these mutations may prove beneficial for the efficient targeting of therapeutic HSV vectors.

Example 5

This example provides a genetic selection approach to identify additional virus mutations to increase infection. Different from above, this selection uses the highly impaired gD receptor TMCΔC derived from nectin-1 in combination with a wild-type gD virus instead of a mutant gD virus.

As described in Example 1, J/TMCΔC cells are gD receptor-deficient J1.1-2 baby hamster kidney cells that stably express a severely debilitated version of the HSV entry receptor nectin-1, and which are used as a target for selection of complementing mutations. The defective receptor, J/TMCΔC, has mutations in the nectin-1 variable (V) domain that reduce gD binding, and lacks the two constant (C) domains of nectin-1. Inoculation of J/TMCΔC cells with K26GFP, a recombinant virus that expresses GFP as a fusion with VP26, yielded no green fluorescence even at an MOI of 1,000. To confirm that this was due to the absence of functional entry receptors, the cells were inoculated with a replication-defective HSV mutant, QOZHG, that expresses lacZ from the ICP0 IE promoter and GFP from the CMV IE promoter, and virus entry was assessed by X-gal staining at 24 hpi. No entry was detected on J/TMCΔC cells, while almost 100% entry was observed at the same virus input (MOI=10) on J cells expressing wild-type nectin-1 (J/C). The same result was obtained by observation of GFP signals. These findings indicated that the J/TMCΔC protein lacked any ability to function as an HSV entry receptor and thus could be a suitable target for the selection of complementing mutations.

J/TMCΔC cells (twenty 10-cm dishes) were inoculated with K26GFP at an approximate MOI of 1,000 and rinsed with 0.1 M glycine (pH 3.0) (referred to hereafter as acidic wash) at 24 h post-infection (pi). Combined intracellular and extracellular virus harvested at 72 hpi (first-round product) was expanded on J/A cells for a second round of infection of J/TMCΔC (twenty 10-cm dishes) at an MOI of approximately 1,000 and acidic wash at 24 hpi. Progeny virus was again harvested and expanded (second-round product). After two more rounds of selection at the same MOI and one round at an MOI of ~300, plaques were purified by limiting dilution on B78/TMC cells expressing full-length TMC. Selected isolates were analyzed by selective sequencing. All mutant sequences reported here were unambiguous, confirming the purity of the isolates and the absence of wild-type virus.

To identify genetic alterations responsible for the ability of the fifth-round products to enter and spread on J/TMCΔC cells, 46 viruses were individually purified by limiting dilution and propagated for DNA extraction. Surprisingly, direct sequencing of the gD ORFs of these isolates demonstrated that only 16 (Nos. 31-46 in Table 2) harbored a missense mutation in this gene, while the remaining 30

(Nos. 1-30) showed no amino-acid changes in this region. Among the 16 isolates with substitutions in gD, 12 had A185T (Nos. 31-42), 3 had S140K (Nos. 43-45), and 1 had S276L (No. 46). A185T and a different substitution at position 140 (S140N) have been described previously (10, 41).

substitutions. Surprisingly, of 7 sequenced isolates, 6 had the same two substitutions (N753K/A778V; Nos. 2-4, 31, 44, 46), while one, harboring both gD:A185T and gB:S668N, showed an A571T substitution in gH (No. 32). These results, particularly the identification of one isolate (No. 1) that carried the gH:N753K/A778V double mutation as the only

TABLE 2

Mutations in selected virus isolates[a]

| No.[b] | gB[d] | gH[e] | gL[e] | No.[b] | gD[c] | gB[d] | gH[e] | gL[e] |
|---|---|---|---|---|---|---|---|---|
| 1 | wt | wt | N753K/A778V | wt | 24 | wt | | | |
| 2 | wt | S 668N | N753K/A778V* | | 25 | wt | | | |
| 3 | wt | Hinc(-) | N753K/A778V* | | 26 | wt | | | |
| 4 | wt | Hinc(+) | N753K/A778V* | | 27 | wt | | | |
| 5 | wt | Hinc(+) | | | 28 | wt | | | |
| 6 | wt | Hinc(+) | | | 29 | wt | | | |
| 7 | wt | Hinc(+) | | | 30 | wt | | | |
| 8 | wt | Hinc(+) | | | 31 | A185T | wt | N753K/A778V* | |
| 9 | wt | Hinc(+) | | | 32 | A185T | S668N | A571T | |
| 10 | wt | Hinc(+) | | | 33 | A185T | Hinc(-) | | |
| 11 | wt | Hinc(+) | | | 34 | A185T | Hinc(-) | | |
| 12 | wt | Hinc(+) | | | 35 | A185T | Hinc(-) | | |
| 13 | wt | Hinc(+) | | | 36 | A185T | Hinc(-) | | |
| 14 | wt | Hinc(+) | | | 37 | A185T | Hinc(+) | | |
| 15 | wt | Hinc(+) | | | 38 | A185T | Hinc(+) | | |
| 16 | wt | | | | 39 | A185T | Hinc(+) | | |
| 17 | wt | | | | 40 | A185T | Hinc(+) | | |
| 18 | wt | | | | 41 | A185T | Hinc(+) | | |
| 19 | wt | | | | 42 | A185T | Hinc(+) | | |
| 20 | wt | | | | 43 | S140K | Hinc(+) | | |
| 21 | wt | | | | 44 | S140K | Hinc(+) | N753K/A778V* | |
| 22 | wt | | | | 45 | S140K | | | |
| 23 | wt | | | | 46 | S276L | Hinc(+) | N753K1A778V* | |

K26GFP was passaged five times through J/TMCΔC cells and progeny viruses were plaque-purified.
[b]Isolate numbers referred to in the text.
[c]Direct sequencing was performed on the entire gD ORF. Amino acid substitutions are indicated. wt, no substitution.
[d]Results of direct sequencing of the complete gB ORF or diagnostic HincII digestion of PCR amplicons. Amino acid substitutions are indicated. wt, no substitution. Hinc(-), absence of the diagnostic HincII site. Hinc(+), presence of the diagnostic HincII site. Blank, not tested.
[e]Results of direct sequencing of the entire gH and gL ORFs (except for a highly GC-rich 24-nucleotide portion of gH) or *, a portion of the gH locus containing positions 753 and 778. Amino acid substitutions are indicated. wt, no substitution. Blank, not tested.

Since the majority of the virus isolates had no gD mutations, the gB ORFs of one gD:wt (No. 2) were compared with one gD:A185T isolate (No. 32). Direct sequencing revealed that both isolates had acquired an S668N substitution creating a new HincII recognition site in the gB gene. An additional 28 isolates (Nos. 1, 3-15, 31, 33-44, 46) were screened by HincII-digestion of PCR amplicons spanning the mutant position showing that 21 of these (Nos. 4-15, 37-44, 46) contained the new HincII recognition site. The complete gB ORFs of two of the seven HincII-negative isolates were sequenced, one harboring gD:A185T (No. 31) and the other containing wild-type gD (No. 1). No amino acid substitutions were found in either one. Thus, while 23 out of 30 isolates had acquired the gB: S668N substitution, suggesting a role for this mutation in the new phenotype of these isolates, at least one was unchanged in both its gD and gB ORFs.

To identify the change(s) in isolate No. 1 responsible for its ability to enter and form plaques on J/TMCΔC cells, the ORFs in this isolate for the two other essential entry glycoproteins, gH and gL, were sequenced. While no mutations were found in the gL ORF, the nearly complete gH sequence revealed two amino-acid substitutions, N753K and A778V; this sequence excludes a highly GC-rich 24-nucleotide portion of gH that could not be read (positions 2079-2102 in GenBank accession number X03896). Isolates with identified gD and/or gB mutations were then analyzed to determine whether they contained either or both of these gH change in the four essential glycoprotein genes, strongly suggested that this double mutation had imparted the ability of a number of the isolates, perhaps the majority, to grow and form plaques on J/TMCΔC cells.

Example 6

This example demonstrates evaluation of entry into cells for recombinant viruses containing the gH:N753K/A778V and gH:S668N substitutions (referred to hereafter as gH:KV and gH:668N, respectively) separately or in combination.

To separate the gB:668N and gH:KV substitutions from potential other changes in the original isolates, each mutant allele was transferred into a wild-type virus background by standard homologous recombination to obtain recombinants named K-gB:668N and K-gH:KV, respectively. In addition, a double-recombinant virus, K-gB:668N-gH:KV, was established to identify potential combinatorial effects of the gB:668N and gH:KV alleles. Likewise, the double recombinant K-gB:NT-gH:KV was generated containing both the gB:N/T mutant allele described earlier and gH:KV. All of these recombinant viruses were confirmed by DNA sequencing through the entire gB, gD, and gH ORFs except for the highly GC-rich 24-nucleotide portion of gH mentioned earlier. The recombinants, along with wild-type KOS virus and K-gB:N/T described above (referred to here as K-gB: NT), were propagated simultaneously and titered on Vero cells.

K-gB:668N was established by co-transfection of Vero cells with KΔT viral DNA and plasmid pgB1:5668N, followed by plaque purification through three rounds of limiting dilution on Vero cells. Plasmid pgB1:S668N was created by substitution of an S668N-containing gB fragment amplified on DNA from isolate No. 5 for the corresponding fragment of pgB1, a plasmid containing the gB open reading frame (ORF) and flanking regulatory sequences from K26GFP.

K-gH:KV, K-gB:668N-gH:KV, and K-gB:NT-gH:KV were established in two steps. First, KΔgH, K-gB: 668NΔgH, and K-gB:NTΔgH were established by co-transfection of gH-complementing F6 cells with plasmid pΔgH-EGFP and viral DNA of KOS, K-gB:668N, or K-gB:NT, respectively, and purification of green plaques on F6 cells. Plasmid pΔgH-EGFP was created by replacing the sequence of the gH ectodomain and transmembrane region in pgH1: wt, a plasmid that contains the gH ORF and flanking regulatory sequences from KOS, with the EGFP ORF from pEGFP-C1 (Clontech). K-gH:KV, K-gB:668N-gH:KV, and K-gB:NT-gH:KV were then established by co-transfection of Vero cells with plasmid pgH1:N753K/A778V and viral DNA of KΔgH, K-gB:668NΔgH, or K-gB:NTΔgH, respectively, and plaque purification on Vero cells. Plasmid pgH1: N753K/A778V was created by substitution of an N753K/A778V-containing gH fragment amplified on DNA from virus isolate No. 1 for the corresponding fragment of pgH1: wt.

K-gH:KVΔgD, K-gB:668N-gH:KVΔgD, and K-gB:NT-gH:KVΔgD were produced by co-transfection of gD-complementingVD60 cells with plasmid pΔgD-EGFP and viral DNA of K-gH:KV, K-gB:668N-gH:KV, or K-gB: NT-gH:KV, respectively, followed by purification of green plaques on VD60 cells.

All recombinant viruses were confirmed by PCR and DNA sequencing through the relevant glycoprotein genes or deletions.

Entry assays were performed as described above for K-gB:NT.

As shown in Examples 2-3 above, K-gB:NT has the ability to enter CHO-K1 cells, a cell line like J1.1-2 and B78H1 that is resistant to HSV-1 due to the absence of gD receptors. Recombinant viruses harboring gB:668N or gH:KV were assayed to determine whether they shared this ability. Entry of K-gB:NT into CHO-K1 cells was detectable at an MOI of 3 or higher, whereas no entry was seen by wild-type KOS at an MOI of 30 and only limited entry at an MOI of 300. Both K-gB:668N and K-gH:KV reproducibly showed somewhat more entry than wild-type KOS, with K-gH:KV reaching a level that was approximately 10-fold below that of K-gB:NT. The double-recombinant K-gB: 668N-gH:KV yielded at least 10-fold more entry than K-gB: 668N or K-gH:KV, comparable to the level observed for K-gB:NT. Moreover, entry by the second double-recombinant virus, K-gB:NT-gH:KV, exceeded that not only of K-gH:KV, but also that of K-gB:NT. Importantly, all of the mutant viruses entered Vero cells to similar degrees as wild-type KOS, excluding the possibility that the observed differences in entry into CHO-K1 cells were due to viral input differences. Similar trends were recorded on gD-receptor-deficient B78H1 cells. Together, these results indicated that the gB:668N and gH:KV alleles possessed a limited ability to compensate for the absence of authentic gD receptors in virus entry and that gH:KV could act cooperatively with both gB:668N and gB:NT to enhance this ability.

As shown earlier, gB:N/T entry into gD-receptor-deficient CHO-K1 cells still requires gD. To determine if combinations of mutant gB and gH could eliminate the gD dependence of HSV entry, gD-null viruses were prepared from K-gB:668N-gH:KV and K-gB:NT-gH:KV, designated K-gB:668N-gH:KVΔgD and K-gB:NT-gH:KVΔgD, respectively, by replacement of the complete gD ORFs with that of GFP. Virus stocks were prepared by passage through Vero cells to remove the complementing wild-type gD protein provided by VD60 cells. Since gD-null viruses cannot be titered on Vero cells, qPCR was used to determine the genome titers [genome copies (gc)/ml] of these viruses and their gD±counterparts. CHO-K1 cells were then inoculated with each of the viruses at 300 gc/cell and entry was visualized at 8 hpi by immunostaining for ICP4. No entry was observed with either of the gD-null recombinants, demonstrating that gD is indispensable for CHO-K1 infection even when the viruses carry combinations of entry-enhancing gB and gH alleles.

These results show that the gB and gH mutations, separately or together, facilitate gD-dependent virus entry into cells that lack authentic gD receptors. The mechanism may involve gD recognition of minor or cryptic gD receptor(s) expressed on the cells, such as nectin-3.

Example 7

This example demonstrates rate of entry analyses for the K-gH:KV and K-gB:NT-gH:KV recombinant viruses compared to wild-type HSV-1 KOS.

As described at Example 3 above, gB:NT accelerates HSV entry into gD receptor-positive Vero cells. To determine whether the K-gH:KV mutation had a similar effect, Vero cells were incubated for 30 min at 4° C. with wild-type KOS or gD±mutant viruses at 500 pfu per well, washed thoroughly, incubated at 37 or 30° C. for 0-60 min, and extracellular virus was inactivated by low-pH treatment. The cells were then overlaid with methylcellulose-containing media and incubated at 37° C. for 2 days to allow plaque formation. Percent entry was calculated for each virus relative to the number of plaques produced by the same virus after infection for 2 h at 37° C., conditions that yielded approximately equal plaque numbers for all of the viruses. As can be seen in FIG. 3A-B, the double-recombinant K-gB:NT-gH:KV had the fastest entry kinetics at both temperatures, followed by K-gB:NT. At 37° C., KOS showed the slowest rate of entry, but at 30° C., no difference was observed between the dramatically reduced entry rates of KOS and K-gH:KV. In additional experiments, the entry kinetics of K-gB:668N was found to be similar to that of K-gH:KV at both temperatures. These observations paralleled the differences in entry seen on receptor-deficient cells, suggesting that those differences were also due to allele-specific increases in entry rates relative to KOS. It is evident that the absence of authentic gD receptors causes a general reduction in entry kinetics, and thus differences in the entry rates between the viruses affect the total levels of penetration on receptor-deficient cells for an extended period of time (e.g., 6 h as in the entry assays of Example 6) compared to Vero cells (about 1 h, FIG. 3A).

Together, these data support the likelihood that accelerated entry mediated by the new gB and gH alleles played a role in the selection of the original isolates on J/TMCΔC cells.

Example 8

This example demonstrates evaluation of lateral, or (cell-to-cell), virus spread into cells.

To analyze the role of gH mutations in lateral virus spread, donor cells (Vero or VD60) were infected at an MOI of 10 at 37° C. for 2 h to achieve infection of all cells. Viruses used in this experiment were KOS, K-gB:668N, K-gB:NT, K-gH: KV, K-gB:668N-gH:KV, and K-gB:NT-gH:KV. Extracellular virus was then inactivated by acidic wash and the cells were incubated at 37° C. for 1 h, trypsinized, and suspended in fresh culture media. Equal numbers of infected (donor) cells were seeded onto monolayers of uninfected (acceptor) cells in a 48-well plate. After a 3-h incubation at 37° C., the cells were overlaid with methylcellulose-containing medium. Two or three days later, the overlay was removed, and the cells were fixed with 100% methanol and immunostained with monoclonal mouse anti-VP16 antibody (1:400) (Santa Cruz) and Cy3-conjugated sheep anti-mouse IgG (1:400).

Each of the viruses formed plaques on acceptor Vero cells and gD-receptor-transduced B78 cell lines (B78/A, B78/C), regardless of the nature of the gB and gH alleles, although the plaques formed by the three gH:KV-harboring viruses tended to be somewhat larger than the plaques formed by the other viruses. Surprisingly, however, the three viruses harboring gH:KV formed plaques on gD-receptor-negative B78 cells as well (B78/0G, containing a GFP gene controlled by the virus-inducible ICP0 promoter); observation of green fluorescence confirmed that these plaques consisted of infected acceptor cells rather than donor cells. Analysis at higher magnification showed very small green foci in the KOS, K-gB:668N, and K-gB:NT wells, consistent with a single round of virus spread from individual donor cells to their nearest neighbors without subsequent spread between acceptor cells. In contrast, plaques formed by the three gH:KV-harboring viruses showed several layers of fluorescent cells around a vacant space in the middle, indicative of initial virus spread from a central infected Vero cell to its immediate neighbors, followed by multiple rounds of spread from one gD-receptor-negative cell to the next. Similar results were obtained using CHO/0G cells, another gD-receptor-deficient line that expresses GFP in response to virus infection. These observations provided compelling evidence that the gH:KV double mutation enables spread between cells that lack authentic gD receptors. Since neither of the gB mutant alleles displayed a similar ability, this conclusion implies mechanistic differences and differential roles of gB and gH in entry of free virus and entry by cell-to-cell spread.

Next, to determine the requirement for gD in spread of the different gH:KV recombinant viruses on gD-receptor-deficient cells, gD-knockout versions of these viruses were assayed. Infectious center assays were performed as above except that the virus stocks were prepared on gD-complementing VD60 cells and VD60 cells were used as donor cells; plaque formation was recorded after 3 days. VP16 immunostaining showed that the gD-null viruses yielded only single-cell infections or very small foci on gD-receptor-deficient B78H1 cells or receptor-positive Vero cells, indicating that gD is required for cell-to-cell spread regardless of the presence or absence of gD receptors and spread- or entry-enhancing gB/gH mutant alleles in the viruses.

In view of the evidence above that gB:NT, gH:KV, and gB:668N, alone or in combinations, do not complement gD-null viruses in entry, these results demonstrate that the different mutant alleles do not confer a new gD-independent mechanism of virus entry from either the media or neighboring cells. Instead, each of these alleles likely acts by amplifying a weak signal from gD, resulting in effective execution of the fusion reaction.

Example 9

This example demonstrates evaluation of the effect of gH:KV mutant gene on virus replication and egress.

To examine the possibility that increased virus replication, virion assembly or transport to the cytoplasmic membrane played a role in the increased lateral spread of K-gH:KV and/or the original selection of gH:KV-bearing viruses on J/TMCΔC cells, the replication and egress efficiency of K-gH:KV were compared with that of KOS. Vero cells were infected for 1 h at an MOI of 3, extracellular virions were inactivated by acidic wash, and viral titers in cell lysates and media at 4, 8, and 24 hpi were determined separately. As shown in FIG. 4A, the two viruses exhibited similar titers in both compartments at each of the selected time points. Similar results on B78/C cells (FIG. 4B) indicated that this outcome was not dependent on a specific cellular background. These observations argued that the spread-enhancing activity of gH:KV could not be attributed to increases in the efficiency of virus replication or egress.

Transfection of HSV-susceptible cells with the four essential glycoproteins, gB, gD, gH, and gL, causes cell-cell fusion, which is believed to reflect, at least in part, the normal functions of these glycoproteins and their receptors in HSV entry and spread (*J Virol* 72:873-5, 1998; *J Gen Virol* 81:2017-27, 2000; *Virology* 279:313-24, 2001). To examine the ability of gH:KV in combination with gB, gD, and gL to induce fusion of gD-receptor-deficient B78H1 cells, B78H1 cells were co-transfected with expression plasmids for gB (pCAgB:wt), gD (pPEP99), gLpPEP101), and either gH:wt (pPEP100 or gH:KV (pCΔgH:KV), using Lipofectamine2000 (Invitrogen). Transfection of B78H1 cells with the four wild-type genes did not produce detectable cell fusion, in agreement with previous results demonstrating that a gD receptor is essential for HSV glycoprotein-mediated cell fusion (*Virology* 279:313-24, 2001). In contrast, replacement of the wild-type gH plasmid with the gH:KV version yielded readily detectable multinucleated cells indicative of cell-cell fusion. No syncytia were observed on transfection of the same cells with plasmids expressing gB:NT and wild type gD, gH, and gL.

These results indicate that gH:KV, but not gB:NT, facilitates a rate-limiting step in the fusion cascade leading to viral cell-to-cell spread. Together, the distinct properties of gB:NT and gH:KV indicate that these two alleles address separate rate-limiting steps controlling virus entry and lateral spread, respectively.

Example 10

This example demonstrates that hyperactive glycoprotein B mutations augment fully retargeted HSV infection.

To retarget virus entry exclusively to epidermal growth factor receptor (EGFR)-bearing cells, gD residues essential for binding to the natural receptors were mutated or deleted, and EGF or an EGFR-specific single-chain antibody (scFv) were inserted near the amino terminus.

FIG. 5 illustrates modifications in the gD coding sequence designed to detarget HSV from its natural entry receptors and retarget the virus to EGFR. Detargeting mutations included a small (residues 7-11) or larger deletion (residues 2-24) in the HVEM-binding N-terminal region and one or two amino-acid substitutions (Y38C or A3C/Y38C) to ablate virus entry through nectin-1. To retarget these constructs, an scFv directed against EGFR (scEGFR) was inserted in the 2-24 deletion or, as described in Example 4, between residues 24 and 25. In addition, constructs containing the EGF sequence at the same positions were also created.

To assess the complementing activity and specificity of the retargeted gD constructs of FIG. 5 (designated gD:Δ224/38C-EGF, gD:Δ224/38C-scEGFR, gD:3C/Δ711/38C-EGF, and gD:3C/Δ711/38C-scEGFR), transient complementation assays were performed using gD-null viruses that expressed either wild-type gB or the gB:NT mutant allele (K-gB:wtΔgD and K-gB:N/TΔgD described in Example 4). Vero cells were transfected with expression plasmids for the parental detargeted gD genes (gD:Δ224/38C and gD:3C/Δ711/38C, FIG. 5) or the retargeted gD genes and the cells were infected the next day with K-gB:wtΔgD or K-gB:N/TΔgD. Supernatants were harvested the following day and used to infect HSV-resistant baby hamster kidney J1.1-2 cells or J1.1-2 derivatives expressing HVEM (J/A), nectin-1 (J/C), or EGFR (J/EGFR). Results showed that the gD genes harboring the EGFR targeting sequences (EGF or scEGFR) allowed entry of the gB:NT/gD-null virus into J/EGFR cells, but entry of the gB:wt/gD-null virus into these cells was essentially undetectable. In addition, none of the mutant gD constructs allowed entry of either virus into J1.1-2, J/A, or J/C cells whereas the wt gD gene enabled entry of both viruses into J/A and J/C cells.

The same transiently complemented viruses were also tested on Vero cells commonly used for HSV propagation. These cells express simian EGFR endogenously as well as natural gD receptors. Similar to J/EGFR cells, both the EGF- and the scEGFR-retargeted gD genes allowed gB:NT-dependent gD-null virus entry into Vero cells, while no entry was observed in the absence of the EGFR-targeting ligands or by complemented gB:wt/gD-null virus. Unlike J/EGFR cells, however, Vero cells were also susceptible to both viruses complemented with gD:wt, allowing a direct comparison of the relative levels of normal and retargeted virus entry via their respective receptors. This comparison indicated that entry of the gB:NT/gD-null virus complemented with either of the two scEGFR-harboring gD alleles was almost as efficient as entry by gD:wt-complemented gD-null/gB:wt virus.

The scEGFR sequence was also inserted into a deletion of residues 61 through 218 in gD (gD:A61-218-scEGFR), a position used by Menotti and colleagues for the insertion of an anti-HER-2 scFv resulting in efficient virus retargeting to HER-2-expressing cells. Complementation of gB:NT/gD-null or gB:wt/gD-null viruses with the gD:A61-218-scEGFR construct did not yield detectable entry into J/EGFR cells or CHO/EGFR cells, another EGFR-transduced HSV-resistant cell line. Likewise, no entry was observed with EGF inserted into the 61-218 deletion.

Together, these results indicate that (i) the detargeting mutations in both types of constructs (gD:Δ224/38C and gD:3C/Δ711/38C) were effective; (ii) targeting was accomplished not only by scEGFR, but also by the natural receptor ligand, EGF; and (iii) the gB:NT allele raised the efficiency of retargeted infection to a level near that seen with a comparable wt virus entering via the natural HSV receptors. Further, the results imply that the 61-218-deleted version of gD does not represent a universally effective platform for gD retargeting by ligand insertion.

Example 11

This example demonstrates efficiency, specificity, and kinetics of retargeted HSV entry.

The scEGFR-containing gD constructs were used to establish retargeted gB:wt and gB:NT recombinant viruses by homologous recombination with the corresponding gD-null viruses (K-gB:wtΔgD and K-gB:N/TΔgD) on gD-complementing VD60 cells. Recombinants were plaque-purified by multiple rounds of limiting dilution and finally passaged through non-complementing Vero cells to obtain virus preparations free of wild-type gD protein. Absolute virus titers expressed as genome copies (gc)/ml were determined by qPCR for the viral immediate early gene ICP47; these titers allow comparison of the entry efficiencies between viruses that differ in their recognition of entry receptors.

Fluorescence analysis showed that gB:NT recombinant viruses expressing either of the scEGFR-retargeted gD constructs entered J/EGFR cells efficiently, comparable to the entry of parental wt HSV-1 strain KOS into J/A or J/C cells that express authentic HSV receptors. In contrast, the gB:wt versions of these recombinants entered J/EGFR cells some 100-fold less efficiently. None of the retargeted viruses detectably entered into J1.1-2, J/A, or J/C cells even at high virus input (1,000 gc/cell), demonstrating that the detargeting mutations in the retargeted gD constructs were effective in abolishing virus entry via the natural HSV receptors. Similar results were obtained on CHO-K 1 cells and receptor-expressing derivatives. Consistent with these results, the gB:NT version of each of the scEGFR-retargeted viruses entered Vero cells as efficiently as wt KOS virus while the gB:wt versions showed limited entry only at high virus concentrations. Entry of the gB:NT version of the gD:Δ224/38C-scEGFR virus into Vero cells was confirmed to be EGFR dependent by pretreating the cells with anti-EGFR monoclonal antibody (mAb), resulting in a dose-dependent inhibition of entry without effect on entry of wt KOS virus As described above, the gB:NT allele accelerates HSV entry via normal and cryptic receptors, and thus it was of interest to compare the rate of entry of the gB:NT and gB:wt versions of the gD:Δ224/38C-scEGFR virus. Briefly, Vero-derived gD-complementing VD60 cells were infected for 0-60 min, extracellular virus was removed, and plaques were counted 2d later; the use of VD60 cells eliminates differences in gD-dependent lateral virus spread following the initial entry of extracellular virus and thus minimizes differences in the rate of plaque formation by intracellular viruses expressing different gD genes. Wild-type KOS entered VD60 cells gradually over 60 min while the gB:wt version of the retargeted virus entered at a highly reduced rate (FIG. 6). However, the retargeted virus expressing the gB:NT allele entered VD60 cells more rapidly not only than the gB:wt version, but also than wt KOS virus, reaching a plateau value at approximately 20 min.

These results demonstrate that the gB:NT allele dramatically increases the kinetics of retargeted virus entry via a target receptor that bears no relationship to any known common or cryptic HSV receptors.

Example 12

This example demonstrates retargeted virus infection and killing of human tumor lines.

Entry and cell-killing abilities of the gD:Δ224/38C-scEGFR viruses and KOS were compared on a panel of HSV-permissive human tumor lines known to express EGFR, including lung carcinoma A549, colon carcinoma HT29, pancreatic carcinoma BxPC3, glioblastomas U87 and SNB19, and epidermoid carcinoma A431. Inoculation at 10 gc/cell yielded readily detectable entry of the gB:NT version of the retargeted virus, but only minimal entry of the gB:wt version. KOS virus entered each of these cell lines at a similar efficiency as the retargeted gB:NT virus, as observed earlier with Vero cells (FIG. 6). To confirm the receptor specificity of the retargeted virus on HSV-susceptible human cells, HT29 cells were treated with anti-EGFR mAb prior to infection. Dose-dependent inhibition of entry of the retargeted gB:NT virus, but not KOS, was observed.

To assess the oncolytic potential of these retargeted gB:wt and gB:NT viruses, A549 and U87 cells were infected with increasing amounts of the viruses and cell viability was determined by MTT assay at 3 or 6 days post-infection. As shown in FIG. 7, the retargeted gB:NT virus showed efficient cell killing at 10 gc/cell, similar to KOS. However, A549 cells were killed less efficiently by the retargeted virus than by KOS at lower virus input, an observation that may relate to the efficiency of lateral spread which can potentially be enhanced by spread-enhancing mutations such as found in the gH:KV allele described above. As expected, the retargeted gB:wt virus showed less killing activity on both cell lines.

These results show that the retargeted gB:NT virus has oncolytic capabilities comparable to a wild-type virus, although efficiency is likely affected by the targeted cell type.

Example 13

This example demonstrates specificity and oncolytic potency of the retargeted gB:NT virus in vivo.

The EGFR scFv used in retargeted viruses as described herein is specific for human EGFR while wt HSV-1 KOS is neurotoxic in mouse strains such as BALB/c. Thus, neurotoxicity testing in mice was performed as a stringent measure of the specificity of the retargeted gB:NT virus. Groups of four mice were injected intracranially with $5 \times 10^3$ gc KOS or a 100,000-fold higher dose of the retargeted gB:NT virus ($5 \times 10^8$ gc). Of the animals injected with KOS virus, one died on day 6, two on day 7, and one on day 9. In contrast, all four mice injected with the retargeted virus remained alive and symptom-free throughout the 47-day observation period. In a separate experiment, brain sections of injected mice were analyzed for the presence of virus by immunostaining for the viral ICP4 protein. Abundant virus was detected in the brain of a mouse that had died on day 21 after receiving KOS at a dose of $1 \times 10^3$ gc, while little virus was detected in brain sections from a mouse that had been sacrificed on day 37 (no symptoms) after injection of $5 \times 10^8$ gc of the retargeted gB:NT virus. Virus stocks used for these experiments were the same as those used in Example 11, showing comparable infection of HSV-susceptible cells lines expressing human or simian EGFR by equal amounts of KOS and the retargeted virus, strongly arguing against the possibility that the observed differences in neurotoxicity between these two viruses were due to dosing errors. Thus, the results confirmed that the retargeted gB:NT virus was effectively detargeted from its natural receptors in mouse brain and was harmless in this complex in vivo environment lacking the targeted receptor.

Next, the retargeted gB:NT virus was examined to determine whether it would preferentially accumulate in EGFR-positive human tumors in nude mice. Following the establishment of subcutaneous U87 flank tumors (700-1,000 mm$^3$), equal gc of KOS and the retargeted gB:NT virus were administered by tail-vein injection. The animals were sacrificed 2 days later and the amount of virus in the tumor and various organs determined by qPCR for the viral ICP4? gene. As shown in FIG. 8A, the number of KOS genomes per 100 ng tissue DNA was lower in the tumors than in the liver, spleen or intestine of the same animals, but comparable to the low numbers in other organs. In contrast, the retargeted virus was detected at 100-1,000-fold higher levels or more in the tumors than in other tissues. These results clearly demonstrate that the retargeted virus preferentially homed to the human tumor tissue.

To examine the anti-tumor efficacy of the retargeted gB:NT virus, U87 flank tumors averaging approximately 140 mm$^3$ in size were injected with PBS or virus at $5 \times 10^8$ gc. As shown in FIG. 8B, PBS-injected tumors increased in size to 900-1,000 mm$^3$ over a period of 29 days, whereas the growth of tumors injected with the retargeted virus was suppressed during the first 20 days, resulting in only a limited increase in size at the end of the observation period (FIG. 8B).

While these results indicate that a single injection of the retargeted virus was not sufficient for complete tumor eradication, they provide compelling evidence of effective tumoricidal activity without adverse effects attributable to the virus.

Example 14

This example demonstrates HSV vector targeting to carcinoembryonic antigen (CEA), a cell surface molecule frequently overexpressed in human cancers.

A CEA-retargeted gD gene, gD:Δ224/38C-scCEA, was created by inserting the coding sequences of the F39 anti-CEA scFv (scCEA, 238 amino acids) into the 2-24 deletion of gD:Δ224/38C (FIG. 9) and was tested for transient complementation of K-gB:wtΔgD and K-gB:NTΔgD on CHO cells expressing CEA or EGFR. The scCEA in gD was found to enable entry of the gB:NTΔgD virus into CHO-CEA, but not CHO-EGFR cells, and no entry into either cell line was detected for the complemented gB:wtΔgD virus. As controls, the scEGFR-retargeted gD:Δ224/38C construct efficiently complemented K-gB:NTΔgD, but not K-gB:wtΔgD, on CHO-EGFR cells.

Recombinant viruses were then prepared with the CEA-retargeted gD allele and examined for CEA-dependent entry into CEA-positive MKN45 and CEA-negative MKN74 human gastric carcinoma cells. KOS entered into both cell lines, consistent with previous observations (Mol. Ther. 19, 507-514, 2011), but the retargeted viruses entered only into MKN45 cells. More entry into MKN45 cells was observed with the gB:NT version of the scCEA virus than with the gB:wt version, although the difference was not as dramatic as that seen with the scEGFR viruses, and entry by the gB:NT version did not quite reach the level of KOS entry.

These results demonstrate that ligands other than for EGFR can be inserted into gD:Δ224/38C to accomplish efficient infection through different non-HSV receptors in combination with the gB:NT allele. It is expected that the efficiency of retargeted infection relative to KOS will vary with factors such as the receptor/ligand pair, including the abundance and nature of the targeted receptors.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of killing a cancerous cell in vivo comprising contacting the cell with a mutant HSV vector comprising a modified glycoprotein B (gB) wherein,
   when the parental HSV vector is HSV1 K26GFP, the modified gB comprises a substitution at amino acid residues gB:D285 and gB:A549 or
   when the parental HSV vector is a homologous HSV-1 or HSV-2 vector, the modified gB comprises a substitution at amino acid residues gB:D285 and gB:A549 of the homologous HSV vector, wherein the gB:D285 residue correlates to X in VYPYXEFVL (SEQ ID NO:1) of HSV1 K26GFP and the gB:A549 residue correlates to X in KLNPNXIAS (SEQ ID NO:2) of HSV1 K26GFP, wherein the mutant HSV vector is administered intratumorally, and wherein the mutant HSV vector further comprises a non-native ligand capable of specifically binding epidermal growth factor receptor (EGFR) or carcinoembryonic antigen (CEA) incorporated into the viral envelope of the mutant HSV vector.

2. The method of claim 1, wherein the substitution at gB:D285 is gB:D285N and the substitution at gB:A549 is gB:A549T.

3. The method of claim 1, wherein the mutant HSV vector further comprises an exogenous expression cassette.

4. The method of claim 3, wherein the expression cassette comprises a target sequence for a cellular microRNA.

5. The method of claim 1, wherein the non-native ligand is incorporated into a viral envelope glycoprotein of the mutant HSV vector.

6. The method of claim 5, wherein the viral envelope glycoprotein is gD or gC.

7. A method of killing a cancerous cell comprising contacting the cell with a mutant HSV vector comprising a modified glycoprotein B (gB) wherein,
   when the parental HSV vector is HSV1 K26GFP, the modified gB comprises a substitution at amino acid residues gB:D285 and gB:A549 or
   when the parental HSV vector is a homologous HSV-1 or HSV-2 vector, the modified gB comprises a substitution at amino acid residues gB:D285 and gB:A549 of the homologous HSV vector, wherein the gB:D285 residue correlates to X in VYPYXEFVL (SEQ ID NO:1) of HSV1 K26GFP and the gB:A549 residue correlates to X in KLNPNXIAS (SEQ ID NO:2) of HSV1 K26GFP, wherein the cancerous cell is in vitro.

8. The method of claim 7, wherein the substitution at gB:D285 is gB:D285N and the substitution at gB:A549 is gB:A549T.

9. The method of claim 7, wherein mutant HSV vector further comprises an exogenous expression cassette.

10. The method of claim 9, wherein the expression cassette comprises a target sequence for a cellular microRNA.

11. The method of claim 7, wherein mutant HSV vector further comprises a non-native ligand capable of specifically binding a surface component of a predetermined cell type.

12. The method of claim 11, wherein the predetermined cell type is a cancer cell.

13. The method of claim 11, wherein the non-native ligand is incorporated into a viral envelope glycoprotein of the mutant HSV vector.

14. The method of claim 13, wherein the viral envelope glycoprotein is gD or gC.

15. The method of claim 13, wherein the component is a protein selected from the group consisting of EGFR, EGFRvIII, CEA, and ClC-3/annexin-2/MMP-2.

* * * * *

UNITED STATES PATENT AND TRADEMARK OFFICE
CERTIFICATE OF CORRECTION

PATENT NO. : 11,419,926 B2
APPLICATION NO. : 16/417254
DATED : August 23, 2022
INVENTOR(S) : Joseph C. Glorioso, III, Hiroaki Uchida and Justus B. Cohen It is certified that error appears in the above-identified patent and that said Letters Patent is hereby corrected as shown below:

In the Specification

Column 1, Lines 26-29, please delete "This invention was made with Government support under Grant Numbers CA119298, NS40923, and DK044935 awarded by the National Institutes of Health. The Government has certain rights in this invention." and add "This invention was made with government support under CA119298, NS040923, and DK044935 awarded by the National Institutes of Health. The government has certain rights in the invention.".

Signed and Sealed this
Eleventh Day of November, 2025

John A. Squires
*Director of the United States Patent and Trademark Office*